United States Patent
Dizio et al.

(10) Patent No.: US 10,940,233 B2
(45) Date of Patent: Mar. 9, 2021

(54) FIBRINOGEN COMPOSITION, METHOD AND WOUND ARTICLES

(71) Applicant: 3M INNOVATIVE PROPERTIES COMPANY, Saint Paul, MN (US)

(72) Inventors: James P. Dizio, Saint Paul, MN (US); Zhicheng Tian, Woodbury, MN (US); Jason W. Bjork, Cottage Grove, MN (US); Amy S. Determan, Mahtomedi, MN (US); Robert A. Asmus, Hudson, WI (US); Jonathan J. O'Hare, Oakdale, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 76 days.

(21) Appl. No.: 16/338,803

(22) PCT Filed: Oct. 4, 2017

(86) PCT No.: PCT/US2017/055015
§ 371 (c)(1),
(2) Date: Apr. 2, 2019

(87) PCT Pub. No.: WO2018/067622
PCT Pub. Date: Apr. 12, 2018

(65) Prior Publication Data
US 2020/0038546 A1 Feb. 6, 2020

Related U.S. Application Data

(60) Provisional application No. 62/404,507, filed on Oct. 5, 2016.

(51) Int. Cl.
*A61L 26/00* (2006.01)
(52) U.S. Cl.
CPC ......... *A61L 26/0042* (2013.01); *A61L 26/008* (2013.01); *A61L 2300/418* (2013.01)
(58) Field of Classification Search
None
See application file for complete search history.

(56) References Cited

U.S. PATENT DOCUMENTS

| | | | |
|---|---|---|---|
| 2,492,458 A | 12/1949 | Bering, Jr. |
| 2,736,721 A | 2/1956 | Dexter |
| 2,958,608 A | 11/1960 | Barnard |
| RE24,906 E | 12/1960 | Ulrich |
| 3,037,455 A | 6/1962 | Bozimowski |
| 3,389,827 A | 6/1968 | Abere |
| 4,112,213 A | 9/1978 | Waldman |
| 4,158,594 A | 6/1979 | Becker |
| 4,310,509 A | 1/1982 | Berglund |
| 4,323,557 A | 4/1982 | Rosso |
| 4,427,650 A | 1/1984 | Stroetmann |
| 4,442,655 A | 4/1984 | Stroetmann |
| 4,453,939 A | 6/1984 | Zimmerman |
| 4,472,480 A | 9/1984 | Olson |
| 4,548,736 A | 10/1985 | Muller |
| 4,595,001 A | 6/1986 | Potter |
| 4,710,270 A | 12/1987 | Sunden |
| 4,833,179 A | 5/1989 | Young |
| 4,871,812 A | 10/1989 | Lucast |
| 4,931,282 A | 6/1990 | Asmus |
| 5,088,483 A | 2/1992 | Heinecke |
| 5,120,781 A | 6/1992 | Johnson, Jr. |
| 5,160,315 A | 11/1992 | Heinecke |
| 5,214,119 A | 5/1993 | Leir |
| 5,225,473 A | 7/1993 | Duan |
| 5,389,376 A | 2/1995 | Duan |
| 5,409,966 A | 4/1995 | Duan |
| 5,531,855 A | 7/1996 | Heinecke |
| 5,849,325 A | 12/1998 | Heinecke |
| 5,908,693 A | 6/1999 | Delgado |
| 5,989,215 A | 11/1999 | Delmotte |
| 6,074,663 A | 6/2000 | Delmotte |

(Continued)

FOREIGN PATENT DOCUMENTS

| | | |
|---|---|---|
| CA | 2288539 | 5/2000 |
| EP | 1695724 | 8/2006 |

(Continued)

OTHER PUBLICATIONS

"Hofmeister Series", From Wikipedia—The Free Encyclopedia, [retrieved from the internet on May 28, 2019], URL <http://en.wikipedia.org/wiki/Hofmeister_series>, 2 pages.
Conductivity Ordering Guide, 1999, 2 pages.
Dastjerdi, "Cohesive Behavior of Soft Biological Adhesives: Experiments and Modelling", Acta Biomaterialia, Sep. 2012, vol. 8, No. 9, pp. 3349-3359.
Electrical Conductivity of Aqueous Solutions, 1 page.
Janmey, "Fibrin Gels and Their Clinical and Bioengineering Applications", Journal of the Royal Society Interface, Jan. 2009, vol. 6, No. 30, pp. 1-10.

(Continued)

*Primary Examiner* — Christina Bradley
(74) *Attorney, Agent, or Firm* — 3M Innovative Properties Company; Trisha D. Adamson (57) ABSTRACT

Provided is a method of forming a fibrinogen hydrogel composition, the method including providing a fibrinogen hydrogel or precursor thereof, comprising fibrinogen hydrogel forming salt. The fibrinogen hydrogel forming salt concentration is greater than or equal to the threshold concentration to form a fibrinogen hydrogel. The method further includes denaturing the fibrinogen hydrogel such as by heating. The method optionally further includes combining the fibrinogen hydrogel with a carrier material. When present, the concentration of the carrier material typically ranges from 0.1 to about 50 wt.-%. The method further includes reducing the salt concentration below the threshold concentration to form a fibrinogen hydrogel.

20 Claims, 3 Drawing Sheets

(56) References Cited

U.S. PATENT DOCUMENTS

| | | | |
|---|---|---|---|
| 6,083,856 | A | 7/2000 | Joseph |
| 6,171,985 | B1 | 1/2001 | Joseph |
| 6,198,016 | B1 | 3/2001 | Lucast |
| 6,264,976 | B1 | 7/2001 | Heinecke |
| 6,310,267 | B1 | 10/2001 | Rapp |
| 6,441,092 | B1 | 8/2002 | Gieselman |
| 6,486,377 | B2 | 11/2002 | Rapp |
| 6,500,427 | B1 | 12/2002 | Heimburger |
| 6,503,527 | B1 | 1/2003 | Whitemore |
| 6,503,731 | B2 | 1/2003 | Marx |
| 6,518,343 | B1 | 2/2003 | Lucast |
| 6,548,727 | B1 | 4/2003 | Swenson |
| 6,552,172 | B2 | 4/2003 | Marx |
| 6,599,515 | B1 | 7/2003 | Delomtte |
| 6,699,484 | B2 | 3/2004 | Whitemore |
| 6,965,014 | B1 | 11/2005 | Delmotte |
| 7,407,709 | B2 | 8/2008 | Zhou |
| 7,714,107 | B2 | 5/2010 | Yayon |
| 8,193,317 | B2 | 6/2012 | Yayon |
| 8,273,372 | B2 | 9/2012 | Dye |
| 8,445,009 | B2 | 9/2013 | MacPhee |
| 8,529,941 | B2 | 9/2013 | Hakimimehr |
| 8,618,258 | B2 | 12/2013 | Yayon |
| 9,072,681 | B2 | 7/2015 | Hakimimehr |
| 9,278,155 | B2 | 3/2016 | Asmus |
| 2001/0025154 | A1 | 9/2001 | Rapp |
| 2007/0148474 | A1 | 6/2007 | Lier |
| 2008/0033333 | A1 | 2/2008 | MacPhee |
| 2010/0291219 | A1 | 11/2010 | Karp |
| 2011/0071079 | A1* | 3/2011 | Ameer ............... A61K 38/39 514/9.3 |
| 2011/0206923 | A1 | 8/2011 | Liu |
| 2011/0206924 | A1 | 8/2011 | Liu |
| 2011/0212325 | A1 | 9/2011 | Determan |
| 2013/0040073 | A1 | 2/2013 | Pett |
| 2015/0030580 | A1* | 1/2015 | Seliktar ............... A61L 27/18 424/94.5 |
| 2015/0297806 | A1 | 10/2015 | Hakimimehr |
| 2016/0024141 | A1 | 1/2016 | Issa |

FOREIGN PATENT DOCUMENTS

| | | |
|---|---|---|
| WO | WO 1997-044015 | 11/1997 |
| WO | WO 1999-25782 | 5/1999 |
| WO | WO 2002-089868 | 11/2002 |
| WO | WO 2003-035115 | 5/2003 |
| WO | WO 2004-067704 | 8/2004 |
| WO | WO 2007-144644 | 12/2007 |
| WO | WO 2008-036255 | 3/2008 |
| WO | WO 2009-083544 | 7/2009 |
| WO | WO 2009-120433 | 10/2009 |
| WO | WO 2010-058132 | 5/2010 |
| WO | WO 2010-136818 | 12/2010 |
| WO | WO 2014-209620 | 12/2014 |
| WO | WO 2015-097687 | 7/2015 |
| WO | WO 2015-124732 | 8/2015 |
| WO | WO 2016-160541 | 10/2016 |
| WO | WO 2018-067628 | 4/2018 |

OTHER PUBLICATIONS

Laurens, "Fibrin Structure and Wound Healing", Journal of Thrombosis and Haemostasis, Apr. 2006, vol. 4, No. 5, pp. 932-939.

Molyneux, Water-Soluble Polymers: Properties and Behavior, 151-152, (1983).

Morena-Arotzena, "Characterization of Fibrin and Collagen Gels of Engineering Wound Healing Models," Materials (Basel), Apr. 2015, vol. 8, No. 4, pp. 1636-1651.

Plasdone povidones, Ashland, 4 pages.

Polyvinylpyrolidone (PVP) Plolymer, Ashland Technical Information, Bulletin VC-843, 9 pages.

International Search Report for PCT International Application No. PCT/US2017/55015, dated Jan. 8, 2018, 3 pages.

* cited by examiner

FIBRINOGEN COMPOSITION, METHOD AND WOUND ARTICLES

CROSS REFERENCE TO RELATED APPLICATIONS

This application is a national stage filing under 35 U.S.C. 371 of PCT/US2017/055015, filed Oct. 4, 2017, which claims the benefit of U.S. Provisional Application No. 62/404,507, filed Oct. 5, 2016, the disclosures of which are incorporated by reference in their entirety herein.

SUMMARY

In one embodiment, a method of forming a fibrinogen hydrogel composition is described. The method comprises providing a fibrinogen hydrogel or precursor thereof, comprising fibrinogen hydrogel forming salt. The fibrinogen hydrogel forming salt concentration is greater than or equal to the threshold concentration to form a fibrinogen hydrogel. The method further comprises denaturing the fibrinogen hydrogel such as by heating. The method optionally further comprises combining the fibrinogen hydrogel with a carrier material. When present, the concentration of the carrier material typically ranges from 0.1 to about 50 wt.-%. The method further comprises reducing the salt concentration below the threshold concentration to form a fibrinogen hydrogel. The step of reducing the salt concentration can occur before and/or after combining the fibrinogen hydrogel with the carrier material. The fibrinogen hydrogel precursor may comprise an aqueous solution comprising fibrinogen and a fibrinogen hydrogel forming salt. The salt typically comprises a sodium citrate optionally in combination with NaCl. The threshold salt concentration of the aqueous solution is at least 0.45 wt.-%, or 0.50 wt.-%, or 0.6 wt.-%, or 0.7 wt.-%, or 0.8 wt.-% or 0.9 wt.-%. In some embodiments, the aqueous solution further comprises a fibrinogen hydrogel plasticizer.

In another embodiment, a fibrinogen composition is described comprising a denatured fibrinogen hydrogel having a fibrinogen concentration ranging from 0.1 to 15 wt.-%; optional carrier material, and a fibrinogen hydrogel forming salt. When present, the concentration of the carrier material typically ranges from 0.1 to about 50 wt.-%. The fibrinogen hydrogel forming salt has a concentration less than a threshold concentration to form the fibrinogen hydrogel. In typical embodiments, the denatured fibrinogen hydrogel is at least partially dehydrated.

In another embodiment, a fibrinogen composition is described comprising a dehydrated denatured fibrinogen hydrogel and salt at a concentration no greater than 20 wt.-%. The dehydrated denatured fibrinogen composition may optionally be interdispersed with 0.5 to 99 wt.-% of a carrier material.

The dehydrated denatured fibrinogen hydrogel composition typically has a salt concentration no greater than 20, 15, 10, or 5 wt.-%. The dehydrated denatured fibrinogen hydrogel or fibrinogen composition can be in various physical forms such a sheet, foam, or plurality of pieces.

The carrier material is typically not water, fibrinogen hydrogel plasticizer, or mixture thereof. In some embodiments, the carrier material is a polymer. The carrier material may optionally further comprise a swelling agent and/or a modifying polymer.

In another embodiment, a method of forming a fibrinogen article is described comprising providing a (e.g. dehydrated) denatured fibrinogen composition as described herein and disposing the composition on or within a carrier layer, such as a skin adhesive, release liner, a polymeric film, a polymeric foam, or a nonwoven or woven fibrous material.

In other embodiments, wound dressings are described comprising a (e.g. dehydrated) denatured fibrinogen composition as described herein alone or in combination with a carrier material.

In another embodiment, a method of treatment of a wound is described comprising providing a (e.g. dehydrated) denatured fibrinogen composition or wound dressing as described herein, and providing the composition proximate a wound. The fibrinogen composition can increase the rate of re-epithelialization and/or wound healing biological markers such as VEGF, EGF, MMP1, MMP8, MMP9, and TIMP-1.

DETAILED DESCRIPTION

In one embodiment, a method of forming a fibrinogen hydrogel composition is described. Fibrinogen is a precursor to fibrin. As used herein, "fibrin" refers to a protein formed by the reaction of fibrinogen with a fibrin-forming enzyme (e.g. thrombin). Such enzyme is capable of cleaving fibrin A and B peptides from fibrinogen and convert it to fibrin.

The method comprises providing a fibrinogen hydrogel or precursor thereof, comprising fibrinogen hydrogel forming salt.

The precursor thereof typically comprises an aqueous solution comprising fibrinogen and salt.

The aqueous solution generally comprises a sufficient amount of fibrinogen. In some embodiments, the amount of fibrinogen in the aqueous solution is at least 5, 6, 7, 8, 9, or 10 wt.-% and typically no greater than about 15 wt.-%. At concentrations of 15 wt-.% and greater, the viscosity can become undesirably high.

The viscosity of the aqueous solution of fibrinogen is typically at least 50 or 100 cps and no greater than about 1000 cps. In some embodiments, the viscosity is less than 900, 800, 700, 600, or 500 cps.

Aqueous solutions of fibrinogen typically comprise salt (e.g. saline). The salt concentration is sufficient such that the fibrinogen forms a solution. Alternatively, solid fibrinogen can be reconstituted in saline or other salt solution.

The aqueous solution further comprises salt suitable for producing a fibrinogen containing hydrogel. Thus, such salt can be characterized as a fibrinogen hydrogel forming salt. The fibrinogen is generally uniformly dispersed and soluble in the hydrogel. Hence, the hydrogel typically contains little or no fibrinogen precipitates. When a fibrinogen hydrogel is formed, the hydrogel is generally a continuous two-phase system that can be handled as a single mass.

Various salts with Group I and/or Group II metal cations have been utilized to solubilize protein such as potassium, sodium, lithium, magnesium, and calcium. Other cations utilized in protein synthesis include citrate, ammonium and guanidinium.

Various anions have also been utilized to solubilize protein. Although chloride anion is most common, nitrate and acetate are most similar to chloride according to the Hofmeister series, i.e. a classification of ions in order of their ability to salt out (e.g. precipitate) or salt in (e.g. solubilize) proteins.

In some embodiments, the salt comprises sodium chloride. The amount of sodium chloride in the aqueous solution and fibrinogen hydrogel, prior to dehydration, is typically greater than 0.09 wt.-% of the solution. The concentration of sodium chloride may be at least 0.10, 0.20, 0.30, 0.04, 0.50, 0.60, 0.70, 0.80 or "normal saline" 0.90 wt.-% and typically no greater than 1 wt.-%. Minimizing the salt concentration is amenable to minimizing the salt that is subsequently removed.

The salt typically comprises a calcium salt, such as calcium chloride. The amount of calcium salt in the aqueous solution and fibrinogen hydrogel, prior to dehydration, is typically at least 0.0015%, 0.0020%, or 0.0030% wt.-% and typically no greater than 0.5 wt.-%.

In some embodiments, the salt comprises sodium citrate (i.e. trisodium citrate $Na_3C_6H_5O_7$). Commercially available fibrinogen can contain sodium citrate. The amount of sodium citrate can be at least 1, 2, 3, 4, or 5 wt.-% solids ranging up to 10, 11, 12, 13, 14 or 15 wt.-% solids. Commercially available fibrinogen can also contain sodium chloride. The amount of sodium chloride can be at least 1, 2, 3, 4, or 5 wt.-% solids ranging up to 10, 11, 12, 13, 14, or 15 wt.-% solids.

In some embodiments, a buffering agent may be present to maintain the desired pH range. In some embodiments, the pH ranges from 6 to 8 or 7 to 8 during the formation of the fibrinogen. Various buffering agent are known. Buffering agents are typically weak acids or weak bases. One suitable buffering agent is a zwitterionic compound known as HEPES (4-(2-hydroxyethyl)-1-piperazine ethanesulfonic acid). Other buffering agents, such as those commonly known as Good buffers can also be utilized. In some embodiments, the buffering agent does not substantially contribute to the formation of the fibrinogen hydrogel. For example when the salt contains sodium and calcium chloride, the buffering agent HEPES does not substantially contribute to the formation of the fibrinogen hydrogel. This means that a fibrinogen hydrogel can be formed with the sodium and calcium salts in the absence of HEPES. Thus the concentration of HEPES in this example, as well as any other salt that does not substantially contribute to the formation of the fibrinogen hydrogel, is not included in the threshold concentration to form a fibrinogen hydrogel. However, HEPES as well as any other salt that does not substantially contribute to the formation of the fibrinogen hydrogel can contribute to the total salt concentration of the dehydrated fibrinogen hydrogel or fibrinogen composition in the event such salts are present after reducing the salt concentration, such as by rinsing.

In some embodiments, the threshold concentration to form a fibrinogen hydrogel is greater than 0.423 wt.-%. The threshold concentration of salt to form a gel may be least 0.430 wt.-% or 0.440 wt.-%, and in some embodiments at least 0.450, 0.500, 0.550, 0.600, 0.650, 0.700, 0.750, 0.800, 0.850, or 0.900 wt.-% of the aqueous solution. It is appreciated that the threshold concentration may vary to some extent depending on the selection of salt(s). In one embodiment, the salt concentration (e.g. $NaCl+Na_3C_6H_5O_7$) is 1.1 wt.-%. However, such salt concentration may be greater than the threshold concentration. The concentration of salt in the (i.e. initially formed) hydrogel is the same as the concentration of salt in the aqueous solution.

When a fibrinogen hydrogel is formed using a threshold concentration of salt and the hydrogel is dehydrated, the resulting dehydrated fibrinogen hydrogel has an even greater concentration of salt. For example, the fibrinogen hydrogel forming salt (e.g. $Na_3C_6H_5O_7$, NaCl, $CaCl_2$) concentration is greater than 10, 15, 20, 25, or 30 wt.-%. As described in US2016/024141, high salt concentrations can cause (e.g. dermal) tissue irritation and damage during the healing process as indicated by inflammatory cell infiltration as well as collagen degeneration and mineralization.

The present method of preparing a fibrinogen composition comprises forming a fibrinogen hydrogel from an aqueous composition as previously described, denaturing the fibrinogen hydrogel, and reducing the salt concentration below the threshold salt concentration to form a denatured fibrinogen hydrogel. For embodiments wherein the (e.g. dehydrated) denatured fibrinogen hydrogel is utilized for wound healing, the method comprises reducing the salt concentration below the concentration that can cause (e.g. dermal) tissue irritation and damage during the healing process.

The most common way of denaturing the fibrinogen hydrogel is by heating. For example, the fibrinogen hydrogel may be heated to a sufficient temperature (e.g. 80° C.) for a sufficient period of time. The denatured fibrinogen hydrogen can exhibit a clear appearance.

In typical embodiments, the step of reducing the salt concentration comprises rinsing the denatured fibrinogen hydrogel alone or in combination with a carrier material with a solution capable of dissolving the salt. The solution is typically aqueous comprising at least 50, 55, 60, 65, 70, 75, 80, 85, 90, or 95 wt.-%, or greater by volume water. The rinsing solution may further contain other water miscible liquids such as plasticizers. The denatured fibrinogen hydrogel is typically rinsed with a volume of solution at least 1, 2, 3, 4, 5, 6, 7, 8, 9, or 10 times greater than the volume of the hydrogel. To reduce the salt concentration even further, the denatured fibrinogen hydrogel may be rinsed with a volume of solution 11, 12, 13, 14, 15, 16, 17, 18, 19, or 20 times greater than the volume of the hydrogel. Another way of reducing the salt includes reacting the cation and/or anion of the salt, or in other words complexing the salt, such that the salt no longer forms ions in an aqueous solution such as bodily fluids of wounds. Another way of reducing the salt concentration is diluting with fibrinogen hydrogel plasticizer and/or by the addition of a carrier material. Further, various combination of these methods can be used.

The amount of fibrinogen hydrogel forming salt (e.g. $NaCl+CaCl_2$) removed from the fibrinogen hydrogel alone or in combination with a carrier material can depend on the amount of salt in the aqueous (e.g. starting) solution and thus, the amount of salt in the initially formed hydrogel. For example, when the aqueous (e.g. starting) solution comprises about 0.9 wt.-% salt, at least about 35 wt.-% of the salt is removed from the fibrinogen hydrogel. However, when the aqueous (e.g. starting) solution comprises about 1.25 wt.-% salt, greater than 50% of the salt is removed from the fibrinogen hydrogel. In some embodiments, at least 40%, 45%, 50%, 55%, 60%, 65%, 70%, 75%, 80%, 85% or 90% of the salt is removed from the hydrogel. In other embodiments, at least 91, 92, 93, 94, 95, 96, 97, 98, or 99% of the salt is removed from the hydrogel. If the threshold concentration is less than 0.9 wt.-%, the amount of salt removed can be less than 35 wt.-%. In such embodiment, at least 5%, 10%, 15%, 20%, 25%, 30%, 35%, 40%, or 45% of the salt is removed from the hydrogel.

The denatured fibrinogen hydrogel alone or in combination with a carrier material having the reduced fibrinogen hydrogel forming salt content is then dehydrated using any number of methods. This step may be referred to as dehydrating, drying or desiccating the hydrogel, all of which refer herein to the process of removing water content from the hydrogel as possible. Dehydration can therefore be accomplished using heat, vacuum, lyophilization, desiccation, filtration, air-drying, and the like. In some embodiments, the dehydrating is accomplished by freeze-drying, oven drying, a low pressure nitrogen steam, or a combination thereof. In some embodiments, lyophilization may be preferred since the resulting fibrinogen material is less likely to swell once in contact with an aqueous solution. However, the oven-dried fibrinogen gel sheets were observed to be more transparent and more uniform than the lyophilized sheets. The dehydration step may occur over a range of time, depending on the particular method used and the volume of the hydrogel. For example, the step may last for a few minutes, a few hours, or a few days. The present disclosure is not intended to be limited in this regard.

The dehydrated denatured fibrinogen hydrogel, optionally further comprising a carrier material, generally has a (e.g. hydrogel forming) salt concentration less than 30 wt.-% or 25 wt.-% (e.g. for a water content of zero ranging up to no greater than 20 wt.-%). When the dehydrated denatured fibrinogen hydrogel as well as the fibrinogen composition is intended for use for wound healing the salt concentration is less than 20, 19, 18, 17, 16, 15, 14, 13, 12, 11, 10, 9, 8, 7, 6, 5, 4, 3, 2, or 1 wt.-% (e.g. for a water content of zero ranging up to no greater than 20 wt.-%). In some embodiments, the dehydrated denatured hydrogel as well as the fibrinogen composition has a water content no greater than 19, 18, 17, 16, 15, 14, 13, 12, 11, 10, 9, 8, 7, 6, 5, 4, 3, 2, or 1 wt.-% or less. In some embodiments, the total salt concentration including the buffering salts are also within the concentration ranges just described. In some embodiments, the dehydrated denatured hydrogel will swell when combined with water (i.e. rehydrated).

The salt concentration of the dehydrated fibrinogen hydrogel, optionally further comprising a carrier material, can be calculated when the kinds and amounts of salt utilized to prepare the fibrinogen hydrogel are known and the salt has not been removed, such as by rinsing with an aqueous solution. The salt concentration of the (e.g. dehydrated) denatured fibrinogen hydrogel composition, optionally further comprising a carrier material, having a reduced salt concentration, can be determine by measuring the conductivity of an aqueous solution containing a specified amount (1% w/w) using a suitable instrument such as a VWR Symphony B30PCI Benctop Multi Parameter Meter—pH, Conductivity, ISE. Quantitative and qualitative analysis of salt can be conducted using ion chromatography, as well as other techniques.

The fibrinogen hydrogel alone or in combination with a carrier material is dehydrated to reduce the water content and thereby increase the fibrinogen concentration. Higher fibrinogen concentrations generally promote healing more rapidly than lower fibrinogen concentrations. The fibrinogen hydrogel, prior to dehydration typically comprises about 0.5 wt.-% to 5, 6, 7, 8, 9, 10, 11, 12, 13, 14 or 15 wt.-% fibrinogen. After dehydration, the fibrinogen composition typically comprises at least 10, 15, 20, 25, 30, 35, 40, 45, or 50 wt.-% fibrinogen. The fibrinogen concentration of the dehydrated fibrinogen hydrogel composition is typically no greater than 99 wt.-% and in some embodiments no greater than 95, 90, 85, or 80 wt.-%.

The dehydrated denatured fibrinogen hydrogel, optionally further comprising a carrier material, typically has a water content of at least 1, 2, 3, 4, or 5 wt.-%. In some embodiments, the dehydrated fibrinogen hydrogel has a water content of at least about 10, 15, or 20 wt.-%. In other embodiments, the water content is no greater than 10 wt.-%.

The (e.g. dehydrated) fibrinogen hydrogel, optionally further comprising carrier material, may include an amount of fibrinogen in a range from 0.1 wt.-% to 10 or 15 wt.-% relative to a total weight. In some embodiments, the (e.g. dehydrated) denatured fibrinogen hydrogel, optionally further comprising carrier material, includes fibrinogen in an amount no greater than 5, 4, 3, 2, 1, 0.1 or 0.05 wt.-%, relative to a total weight of the (e.g. dehydrated) fibrinogen hydrogel.

In some embodiments, the (e.g. dehydrated) fibrinogen hydrogel, optionally further comprising a carrier material, further comprises a plasticizer. Various water-miscible plasticizers are suitable for hydrogels. Such plasticizers typically comprise hydroxyl groups. Suitable plasticizers include for example $C_3$-$C_{24}$ sugar alcohols such as glycerol, diglycerol, triglycerol, xylitol, and mannitol as well as $C_3$-$C_{24}$ alkane diols such as butane diol and propane diol. In some embodiments, the plasticizer comprises an alkylene group having no greater than 12 carbons atoms. The (e.g. dehydrated) fibrinogen hydrogel may contain a single plasticizer or combination of plasticizers. When plasticizer is present, the concentration typically ranges from 0.5 wt.-% to 2 wt.-% of the aqueous starting precursor solution. The dehydrated hydrogel as well as the fibrinogen composition may comprise at least 5, 10, 15 or 20 wt.-% and typically no greater than 80, 70, 60, 50, or 40 wt-% plasticizer.

Inclusion of a plasticizer can result in a flexible dehydrated fibrinogen hydrogel composition, the properties of which can be determined by standard tensile and elongation testing. The film of flexible dehydrated fibrinogen hydrogel for testing can have a thickness of at least 10, 15 or 20 microns and typically no greater than 2 mm, 1 mm, 500 microns, or 250 microns. In some embodiments, the thickness is no greater than 200, 150, 100, 75, or 60 microns. The elongation can range from 10, 15, or 20% to 1000%. In some embodiments, the elongation (e.g. of a 50 micron film) is at least 50% or 75% and no greater than 200%, 150%, or 100%. The ultimate tensile strength is typically at least 0.1, 0.2, or 0.3 MPa and is typically no greater than 150 MPa. In some embodiments, the ultimate tensile strength (e.g. of a 50 micron film) is no greater than 50, 25, 10, or 5 MPa. The Young's elastic modulus is typically at least 0.5, 0.6, 0.7, 0.8, 0.9 or 1 MPa and is typically no greater than about 2000 MPa. In some embodiments, the Young's elastic modulus (e.g. of a 50 micron film) is at least 2 or 3 MPa and typically no greater than 100, 75 or 50 Mpa. Inclusion of the carrier material, especially those containing polymer(s), can also provide fibrinogen films having the tensile and elongation properties just described.

The (e.g. dehydrated) denatured fibrinogen hydrogel, optionally further comprising a carrier material, can include various additives, provided the additives do not detract from forming the fibrinogen hydrogel and reducing the salt concentration therefrom. Examples of additives can include any of antimicrobial agents, anti-inflammatory agents, topical anesthetics (e.g., lidocaine), other drugs, growth factors, polysaccharides, glycosaminoglycans. If an additive is included, it should be included at a level that does not interfere with the activity of the fibrinogen containing layer with respect to promoting healing of the wound.

Antimicrobial agents are agents that inhibit the growth of or kill microbes such as bacteria, mycobacteria, viruses, fungi, and parasites. Anti-microbial agents therefore include anti-bacterial agents, anti-mycobacterial agents, anti-viral agents, anti-fungal agents, and anti-parasite agents. Fibrinogen containing layers so loaded can be used to prevent or control infection.

Anti-inflammatory agents are agents that reduce or eliminate inflammation. Examples include alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, and zomepirac sodium.

The (e.g. dehydrated) denatured fibrinogen hydrogel, optionally further comprising a carrier material, can have various physical forms. In some embodiments, the fibrinogen hydrogel as well as the fibrinogen composition is formed prior to reducing the salt content. The fibrinogen hydrogel as well as the fibrinogen composition is typically sufficiently flowable at a temperature ranging from 0° C. to 37° C. such that the fibrinogen hydrogel takes the physical form of the container surrounding the fibrinogen hydrogel. For, example if the fibrinogen hydrogel as well as the fibrinogen composition is cast into a rectangular pan, the fibrinogen hydrogel as well as the fibrinogen composition forms into a sheet. Thus, the fibrinogen hydrogel as well as the fibrinogen composition can be cast into various shaped containers or in other words molded to provide (e.g. dehydrated) hydrogel of various shapes and sizes.

In one embodiment, the (e.g. dehydrated) denatured fibrinogen hydrogel as well as the fibrinogen composition further comprising the carrier material may be provided as a fibrinogen foam. This can be accomplished by aerating the fibrinogen solution early in the denaturing process. After formation of the fibrinogen foam, salts can then be removed as previously described.

In another embodiment, the (e.g. dehydrated) denatured fibrinogen hydrogel may be provided as particles. For example, (e.g. dehydrated) fibrinogen hydrogel microbeads may be formed, such as by the method described in U.S. Pat. No. 6,552,172 (Marx et al.). In yet another example, (e.g. dehydrated) fibrinogen hydrogel particles may be utilized as microcarriers such as described in US 2010/0291219 (Karp et al.). The salt content of the microbeads and microcarriers is reduced below the threshold concentration to form a fibrinogen hydrogel as previously described. The microbeads and microcarriers can further comprise carrier material as described herein.

In other embodiments, the (e.g. dehydrated) denatured fibrinogen hydrogel, optionally further comprising a carrier material, can be formed after reducing the salt content. For example, a sheet of (e.g. dehydrated) denatured fibrinogen hydrogel optionally further comprising a carrier material, can be (e.g. laser or die) cut into pieces having various shapes and sizes. In another example, the composition may be ground, pulverized, milled, crushed, granulated, pounded, and the like, to produce fibrinogen powder. In some embodiments, methods used for making (e.g. dehydrated) denatured fibrinogen hydrogel particles are typically not dependent on oil-in-water emulsions.

When (e.g. dehydrated) denatured fibrinogen hydrogel composition, optionally further comprising a carrier material, are formed into particles, the method may further involve size separating the particles. This may be accomplished most easily by sieving the particle composition through one or more appropriate sieves or filters having desired pore sizes. In some embodiments the particles can be sieved to arrive at populations having average diameters in the range of about 85-180, 90-170, 100-160, 100-150, 110-150, 120-140, or about 130 micrometers in average diameter. The fibrinogen particles further comprising a carrier material may be equal to or less than 80, 90, 100, 110, 120, 130, 140, 150, 160, 170, or 180 micrometers, provided they have a minimum average diameter of at least 10, 20, 30, 40 or 50 micrometers. It is to be understood that these average diameters refer to the diameter of the dehydrated particles rather than their rehydrated diameters. The particle volume may increase 10-250% of the initial volume after rehydration.

In some embodiments, the (e.g. dehydrated) denatured fibrinogen hydrogel containing particles can be size restricted. In some aspects, the composition comprises a plurality of fibrinogen or fibrinogen composition particles, wherein at least 50% of which have an average diameter of 85-180 micrometers prior to hydration. In some embodiments, at least 55%, at least 60%, at least 65%, at least 70%, at least 75%, at least 80%, at least 85%, at least 90%, at least 95%, or more of the fibrinogen or fibrinogen composition particles have an average diameter of 85-180 micrometers.

The (e.g. dehydrated) denatured fibrinogen hydrogel containing particles may have spherical shape or an irregular non-spherical shape and size. The diameter of a non-spherical particle can be determined by summing its longest and its shortest dimension and dividing that sum by two. This is referred to as the average diameter of a single particle. Average diameter of a population of particles may be deduced based on a sieving analysis (i.e., the sieving analysis would provide a range of average diameters based on retention and/or flow through of particles). It will be understood that the term "average diameter" of a population of particles, defined as "summing its longest and its shortest dimension and dividing that sum by two", is conceptually similar to the term "average particle size", which refers to the "largest dimension" of the particles in a population of the particles.

In some embodiments, (e.g. dehydrated) denatured fibrinogen hydrogel containing particles are provided that are defined by their surface topology, topography, or roughness. The surface topology or roughness may be expressed in terms of the number and/or size of features (or protrusions) on the surface of the particles. Roughness can be observed using techniques commonly used in the art including optical profilometry and atomic force microscopy. The number of features on these particles may range from 2-100 typically. The size of these features (or protrusions) may be expressed in terms of absolute length or in terms of the ratio of the size of the feature (or protrusion) and the average diameter of the particles. In some embodiments, the size of the feature is about 1 micrometer, about 2 micrometers, about 3 micrometers, about 4 micrometers, about 5 micrometers, about 6 micrometers, about 7 micrometers, about 8 micrometers, about 9 micrometers, about 10 micrometers, or more. In other embodiments, the size of the feature is more than 10 micrometers, more than 15 micrometers, more than 20 micrometers, more than 25 micrometers, more than 30 micrometers, more than 35 micrometers, more than 40 micrometers, more than 45 micrometers, more than 50 micrometers, or more. In still other embodiments, the size is 10-100 micrometers. In other embodiments, the size is 1-10 micrometers. The ratio of feature size and particle average diameter may be about 5%, 10%, 15%, 20%, 25%, 30%, 35%, 40%, 45%, or 50%, or more. This surface roughness is important since it has been found that cells such as connective tissue progenitor cells are better able to bind to particles having a greater degree of surface roughness.

In some embodiments, the (e.g. dehydrated) denatured fibrinogen hydrogel containing particles have an average particle size in a range of 0.1 microns up to 100 microns. The fibrinogen particles can have an average particle size, of at least 0.1, 1, 2, 5, or 10 microns. The average particle is typically no greater than 1000 micrometers, 500, 200 or 100 microns.

The (e.g. dehydrated) denatured fibrinogen composition described herein may be utilized in the treatment of a wound.

To facilitate delivery, the (e.g. dehydrated) denatured fibrinogen composition (e.g. particles) may be incorporated into a suitable carrier material to form various fibrinogen-containing gels, pastes, lotions, creams, and ointments. In another embodiment, (e.g. dehydrated) denatured fibrinogen hydrogel particles can be dispersed in a (e.g. aqueous) liquid carrier material (e.g. an emulsion) to form a fibrinogen-containing spray.

The carrier material may be a solid, a liquid, or a mixture of solids and liquids. In some embodiments, the carrier material is not solely water, fibrinogen hydrogel plasticizer, or a combination thereof. However, the carrier material may further comprise water and/or fibrinogen hydrogel plasticizer in combination with another carrier material, such as a polymer.

In typical embodiments, the carrier material may be characterized as physiologically inert, nonionic, and pH stable.

In some embodiments, the carrier material is water soluble. The carrier material may function as a thickener.

The carrier material, particularly in the case of water soluble polymers, such as polyvinyl N-vinyl lactam polymer, can be characterized by their Fikentscher K-value as described in Molyneaux, Water-Soluble Polymers: Properties and Behavior, Vol. 1, CRC Press, 1983, pp. 151-152. In some embodiments, the carrier material can have a Fikentscher K-value of at least K-10, K-15, K20, K-25, K-30, or K35. The Fikentscher K-value of commercially available water soluble polymers typically does not exceed K-120. In some embodiment, the Fikentscher K-value of the carrier material is at least K-40, K-50, K60, K70, K80, or K90.

The carrier material, particularly in the case of polymers, may also be characterized by molecular weight (Mw). In some embodiments, the carrier material has a molecular weight of at least 2,500; 5,000; 10,000; 25,000; or 50,000 g/mole. The molecular weight of the carrier material can range up to 1.5 or 2 million g/mole. In some embodiments, the molecular weight of the carrier material is at least 100,000; 250,000; or 500,000 g/mole.

The K value and molecular weight of the (e.g. polymeric) carrier material can even be higher than the ranges described. For example, the (e.g. polymeric) carrier material can be highly crosslinked such that it is no longer soluble in water at 25° C.

The carrier material, particularly in the case of polymers, may also be characterized by glass transition temperature. In some embodiments, the carrier material has a Tg of at least 120, 125, or 130° C. The Tg of the (e.g. polymeric) carrier material may range up to about 200° C. In some embodiments, the Tg of the carrier material is at least 140, 150, 160, 170, 180 or 190° C. However, the inclusion of swelling agents (e.g. carrier material plasticizer) can reduce the Tg of the carrier material. In this embodiment, the carrier material may have a Tg less than 25° C. or even less than 0° C.

In some embodiments, the carrier material is a film-forming polymer that forms a polymeric matrix. The (e.g. dehydrated) fibrinogen hydrogel may be interdispersed with the carrier material as discrete pieces or particles within the polymeric matrix of the carrier material. Alternatively, the carrier material may be interdispersed with the (e.g. dehydrated) fibrinogen hydrogel as discrete pieces or particles within a polymeric matrix of the (e.g. dehydrated) fibrinogen hydrogel. In other embodiments, the carrier material (e.g. polymer) and the (e.g. dehydrated) fibrinogen hydrogel are interdispersed within a common plasticizer.

In some embodiments, (e.g. dehydrated) denatured fibrinogen particles can be admixed with natural or chemically modified and synthetic biological carrier materials such as collagen, keratin, gelatin, carbohydrates, and cellulose derivatives. Synthetic biological carrier materials can also be utilized such as described in previously cited US 2010/0291219 (Karp et al.).

In some embodiments, the biological carrier material comprises a bioerodible hydrogel such as polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In other embodiments, the biological carrier material is a biodegradable synthetic polymer such as polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxyethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polymers of lactic acid and glycolic acid, polyanhydrides, poly(ortho)esters, polyurethanes, poly(butic acid), poly(valeric acid), and poly(lactide-cocaprolactone) and polyvinylpyrrolidone.

In some embodiments, the biological carrier material comprises an uncrosslinked or crosslinked N-vinyl lactam polymer. Such polymer comprises polymerized units of N-vinyl lactam monomers. Nonlimiting examples of N-vinyl lactam monomers include for example N-vinyl-2-pyrrolidone; N-vinyl-2-valerolactam; N-vinyl-2-caprolactam; and mixtures of any of the foregoing. In some embodiments, the N-vinyl lactam monomer is N-vinyl-2-pyrrolidone. In some embodiments, the poly(N-vinyl lactam) polymer is a homopolymer of N-vinyl-2-pyrrolidone.

In other embodiments, the biological carrier material is a copolymer of N-vinyl lactam. Such copolymers further comprise polymerized units of at least one comonomer. Nonlimiting examples of comonomers include for example N,N-dimethylacrylamide, acrylic acid, methacrylic acid, hydroxyethylmethacrylate, acrylamide, 2-acrylamido-2-methyl-1-propane sulfonic acid or its salt, and vinyl acetate. A single comonomer or combination of comonomers can be employed.

In typical embodiments, the N-vinyl lactam copolymer comprises at least 50, 60, 70, 80, or 90 weight percent of polymerized units of N-vinyl lactam (e.g. N-vinyl-2-pyrrolidone) monomer(s). The N-vinyl lactam copolymer further comprises at least 10, 20, 30, 40, or 50 weight percent of polymerized units of comonomer(s).

Noncrosslinked N-vinyl lactam homopolymer and N-vinyl pyrrolidone/vinyl acetate copolymers are commercially available. Nonlimiting sources of commercially available poly(N-vinyl pyrrolidone) include Aldrich Chemical Co. of Milwaukee, Wis., BASF of Parsippany, N.J., ISP (GAF) of Wayne, N.J., Dan River Corporation of Danville, Va., Spectrum Chemical Manufacturing Corporation of Gardena, Calif., as well as Ashland Inc, Covington, Ky. as "Plasdone™ povidone".

In some embodiments, the (e.g. biological) carrier material comprises a crosslinked polymer. The crosslinked polymer may be any of the previously described natural or synthetic polymers wherein such polymer has been crosslinked. Crosslinking increase the molecular weight and K-value as previously described.

In some embodiments, the crosslinked polymer is a crosslinked synthetic polymer, such as crosslinked poly(N-vinyl lactam). In some embodiments, the (e.g. poly(N-vinyl lactam)) polymer is radiation-crosslinked (i.e. crosslinked by exposure to actinic radiation). The (e.g. poly(N-vinyl lactam)) polymer is typically crosslinked while the polymer in a solid form. In other embodiments, the (e.g. poly(N-vinyl lactam)) synthetic polymer is crosslinked by free-radical polymerization, either in bulk or in solution, of a precursor containing (e.g. N-vinyl lactam) monomer, optionally other monomers, and a crosslinking compound. (See for example, U.S. Pat. No. 4,931,282; incorporated herein by reference.)

The polymer of the solid carrier material can be provided in any form, Nonlimiting examples of solid forms include particles, pellets, sheets, flakes, and bulk objects of various shapes, and coated objects of various shapes. For example U.S. Pat. Nos. 4,931,282; 5,225,473; and 5,389,376, incorporated herein by reference describe solid forms of poly(N-vinyl lactam. Typically, the crosslinked (e.g. poly(N-vinyl lactam)) polymer is in the form of particles having an average particle size (as can be determined by microscopy) of less than about 1, 0.5, 0.25 cm. In some embodiments, the average particle size is less than 1000, 750, or 500 microns. The average particle is typically at about 0.1, 0.5, 1, 2, 3, 4, 5, 6, 7, 8, 9, or 10 microns. In some embodiments, the average particle size is at least 25, 50, 75 or 100 microns. In some embodiments, the average particle size can be reduced during mixing. Alternatively, the polymer of the carrier material can be provided in a liquid form such as (e.g. an aqueous or organic-solvent based) solution, emulsion, or dispersion.

The carrier material can further comprise a swelling agent that can swell the (e.g. gurar) natural or (e.g. poly(N-vinyl lactam) synthetic polymer of the carrier material. In some embodiments, the swelling agent also functions to plasticize the fibrinogen hydrogel. In yet other embodiments, the swelling agent can swell a modifying polymer, also present in the biological carrier material. The swelling agent is biocompatible with human skin.

The polymer of the carrier material can have a Swelling Capacity in water of at least about 15, typically at least about 30, and often at least about 40 as described in U.S. Pat. No. 5,409,966; incorporated herein by reference.

Nonlimiting examples of swelling agents include monohydric alcohols (e.g., ethanol, isopropanol, n-propanol), polyhydric alcohols, (e.g., ethylene glycol, propylene glycol, di propylene glycol, polyethylene glycol (Molecular Weight between 200 and 600) and glycerin), ether alcohols (e.g., glycol ethers), glycerol, polyglycerols (e.g. diglycerin, triglycerol, polyglycerin-3, hexaglycerol and decaglycerol), sorbitol and polyhydric alcohol ethoxylates (e.g. sorbeth-6, sorbeth-30, glycereth-1 to glycereth-31) methoxides of polyethylene glycol (Methoxy PEG-2 to Methoxy PEG 100), methoxides of polyhydric alcohol ethoxylates (e.g. glycereth-7 methoxide), as well as any other (e.g. polyol) swelling agents that do not cause skin irritation or toxic reaction, and water. In some embodiments, the previously described fibrinogen hydrogel plasticizers are utilized as a swelling agent. Various mixtures of swelling agent can also be employed.

Non-volatile and/or volatile swelling agents may be used. Non-volatility for the swelling agent is desired not only at room or body temperatures but also at the elevated temperatures of processing which range from about 75° C. to about 250° C. When the swelling agent in non-volatile, less than ten percent (10%) of a given 50 ml volume, in a 4 oz. jar having a 4 cm diameter circular opening, evaporates after exposure to a temperature of 75° C. for one hour.

The swelling agent may comprise a volatile swelling agent in combination with a non-volatile swelling agent, such as a mixture of glycerin or polyethylene glycol with water. In some embodiments, the carrier material may comprise solely non-volatile swelling agents such as, for example, glycerin or polyethylene glycol. In some embodiments, the carrier material may comprise solely volatile swelling agents such as water. When the carrier material comprises a swellable polymer in combination with bound water, the carrier material may be characterized as a second hydrogel.

The swelling agent is typically a liquid. In some embodiments, humectant-type solid swelling agents like sorbitol could be used in conjunction with a co-swelling agent in order to dissolve the humectant such that it remains in the liquid swelling agent. Other humectants that could also be employed as swelling agents or co-swelling agents include: 1,2,6-hexanetriol, acetamide mea, aluminum hydroxide, arginine pca, butoxypropanol, butylene glycol, dimethyl imidazolidinone, dimethylsilanol hyaluronate, dipotassium glycyrrhizate, erythritol, ethoxydiglycol, fructose, glutamine, gluconic acid, glucose, glucose glutamate, glucuronic acid, glutamic acid, glycogen, glycyrrhizic acid, heilmoor clay, hexacosyl glycol, histidine, hyaluronic acid, hydrogenated honey, hydrogenated starch, hydrolysate, hydrolyzed collagen, hydrolyzed elastin, hydrolyzed glycosaminoglycans, hydrolyzed keratin, hydrolyzed silk, hydrolyzed soy protein, hydrolyzed wheat protein, hydroxyethyl sorbitol, inositol, inositol hexa-pca, lactamide mea, lactic acid, lactitol, lactose, lysine pca, magnesium pca, maltitol, manganese pca, mannitol, mel (honey extract), menthyl pca, methyl gluceth-10, methyl gluceth-20, pca (pidolic acid), lactamide, polydextrose, polyglucuronic acid, polyglyceryl sorbitol, potassium pca, ppg-20 methyl glucose ether, ppg-38-buteth-37, saccharide isomerate, serica, silk amino acids, sodium carboxymethyl chitin, sodium lactate, sodium mannuronate methylsilanol, sodium pca, sodium pca methylsilanol, sodium polyglutamate, soluble collagen, sorbitol, sucrose, tea-lactate, tea-pca, trehalose, trilactin, urea, xylitol, *Zea mays*, zinc pca, and combinations thereof.

The carrier material may comprise a modifying polymer. In some embodiments, the modifying polymer is present to maintain and/or increase cohesiveness while reducing adhesiveness. When added with the swelling agent, the modifying polymer becomes solubulized or suspended in the swelling agent. Typically, the modifying polymer will form a viscous solution or viscous gel when combined with the swelling agent in a ratio of modifying polymer to swelling agent of 1:9.

In some embodiments, the modifying polymer comprises a polysaccharide or derivative thereof, a (meth)acrylate or derivate thereof, or cellulose or a derivative thereof.

Specific examples of modifying polymers include for example hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; and derivatives and combinations thereof.

The concentration of carrier material admixed or interdispersed with the fibrinogen hydrogel can vary depending on the selection of carrier material(s).

In some embodiments, such as prior to dehydration, the denatured fibrinogen hydrogel is combined with a carrier material in an amount of at least 0.5 wt.-% ranging up to about 10 wt.-% of the composition. The carrier material may comprise one or more of the previously described natural or synthetic polymer(s). In some embodiments, the fibrinogen hydrogel comprises a (e.g. poly(N-vinyl lactam) crosslinked synthetic polymer, as a carrier material, in an amount of at least 0.5 or 1.0 wt.-% ranging up to about 4, 5, 6, 7, 8, 9, or 10 wt.-%. Higher concentrations may be used when the synthetic polymer is uncrosslinked. In some embodiments, the fibrinogen hydrogel further comprises a modifying polymer(s) in an amount of at least 0.001, 0.005, or 0.1 wt.-% ranging up to about 1, 1.5 or 2 wt.-%. The fibrinogen hydrogel may further comprise a fibrinogen hydrogel plasticizer and/or swelling agent for the polymer of the carrier material in an amount of at least 0.5 or 1 wt.-% ranging up to 5, 6, 7, 8, 9 or 10 wt.-%. The mixture of fibrinogen hydrogel and carrier may be dispersed in a liquid carrier. The liquid carrier typically comprises a water/alcohol mixture.

The denatured fibrinogen hydrogel and carrier material can be combined with each other in any suitable manner, such as by mixing.

The mixture of denatured fibrinogen hydrogel, carrier material, and liquid carrier can be coated onto a carrier layer, such as foam, using any suitable method including for example dip coating, forward and reverse roll coating, wire wound rod coating and die coating.

After application the liquid carrier, as well as at least a portion of bound water of the hydrogel, is typically removed by dehydration, as previously described.

The dehydrated denatured fibrinogen hydrogel composition may contain little or no water. In some embodiments, the concentration of carrier material can be in the same range as prior to dehydration, as previously described. For example, if the composition initially comprises 2 wt.-% of carrier material and 50 wt.-% of the water is removed, the dehydrated composition contain twice as much, i.e. 4 wt.-%. In other embodiments, the dehydrated fibrinogen hydrogel composition may contain 10 wt.-% to 99 wt.-% of carrier material. However, as the concentration of fibrinogen increases, the concentration of carrier material decreases. Thus, in some embodiments, the carrier material is no greater than 95, 90, 85, 80, 75, 70, 65, 60, 55, 50, 45, 40, 35, 30, 25, 20, 15, 10, 5, or 1 wt.-%.

In some embodiments, the dehydrated denatured fibrinogen hydrogel composition comprises a (e.g. poly(N-vinyl lactam) crosslinked synthetic polymer, as a carrier material, in an amount of at least 15, 20, 25, or 30 wt.-% and typically no greater than 90, 85, 80, 75, 70, 65, 60, 55, or 50 wt.-%. Higher concentration may be useful when the synthetic polymer is uncrosslinked. Likewise, in some embodiments, the concentration of modifying polymer(s) in the dehydrated fibrinogen hydrogel composition can be in the same range as previously described. In other embodiments, the dehydrated fibrinogen hydrogel may contain a concentration ranging from 2 wt.-% to 15 wt.-% of modifying polymer(s). Likewise, in some embodiments, the concentration of fibrinogen hydrogel plasticizer and/or swelling agent for the polymer of the dehydrated fibrinogen hydrogel composition can be in the same range as previously described. In other embodiments, the dehydrated fibrinogen hydrogel may range from 2 wt.-% to 15 wt.-% of fibrinogen hydrogel plasticizer and/or swelling agent for the polymer of the carrier material.

In some embodiments, a carrier material may function as a pressure sensitive adhesive composition suitable for adhering to a wound.

In yet another embodiment, (e.g. dehydrated) denatured fibrinogen particles as described herein can be admixed with various (e.g. acrylic or silicone) skin adhesives to form a fibrinogen-containing skin adhesives.

In typical embodiments, (e.g. dehydrated) denatured fibrinogen hydrogel is provided on or within a carrier layer at a coating weight that is sufficient to provide the desired effect (e.g. promoting wound re-epithelialization). In some embodiments, the coating weight of the (e.g. dehydrated) fibrinogen hydrogel is typically at least 0.2, 0.5, 1, 2, 3, 4, or 5 milligram per $cm^2$ and typically no greater than 30, 35, 20, 25, 20, 15, 10 or 5 milligrams per $cm^2$.

The (e.g. dehydrated) fibrinogen hydrogel composition described herein may be utilized as a wound dressing article. The wound dressing article described herein comprises a (e.g. dehydrated) fibrinogen composition in a suitable physical form such as a sheet (i.e. film), foam sheet, or fibrinogen (e.g. particles) disposed on or within a carrier layer. Thus, the (e.g. dehydrated) fibrinogen hydrogel layer can be provided in various forms as a continuous or discontinuous layer.

In some embodiments, the (e.g. dehydrated) fibrinogen hydrogel composition is formed prior to combining the (e.g. dehydrated) fibrinogen hydrogel composition with a carrier material or carrier layer. In other embodiments, a carrier layer is combined with the aqueous solution comprising fibrinogen and fibrinogen hydrogel forming salt or the fibrinogen hydrogel prior to reducing the salt and/or dehydration. For example, a fibrous (e.g. woven or nonwoven) substrate may be placed in a rectangular pan prior to adding the fibrinogen hydrogel thereby forming a sheet of fibrin hydrogel having a fibrous scrim embedded within the hydrogel. FIGS. 1-10 as follow illustrative some typical wound dressings articles.

Figure 1:
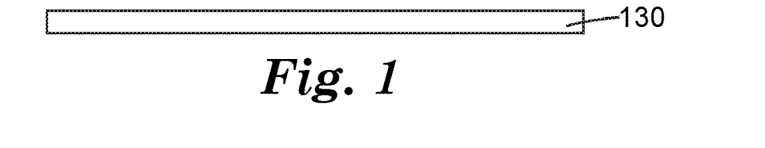
FIG. 1 is a schematic cross-section of an illustrative embodiment of a fibrinogen article suitable for a wound dressing comprising a fibrinogen composition in the form of a sheet.

FIG. 1 illustrates an embodiment of a fibrinogen article, suitable for use as a wound dressing. The fibrinogen article includes a (e.g. flexible) sheet 130 comprising or consisting of the (e.g. dehydrated) fibrinogen gel composition.

Figure 2:
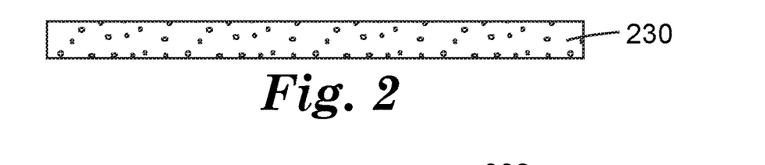
FIG. 2 is a schematic cross-section of an illustrative embodiment of a fibrinogen article suitable for a wound dressing comprising a fibrinogen composition in the form of a sheet of foam.

FIG. 2 illustrates another embodiment of a fibrinogen article, suitable for use as a wound dressing. The fibrinogen article includes a sheet of foam 230 comprising or consisting of the (e.g. dehydrated) fibrinogen gel composition. The foam may having various other shapes formed for example by molding the fibrinogen hydrogel composition (e.g. prior to hydrating) or cutting the foam into pieces after it is formed.

The fibrinogen sheet articles, such as illustrated in FIGS. 1 and 2 typically have a thickness of at least 10, 15 or 20 microns and typically no greater than 2 mm, 1 mm, 500 microns, or 250 microns. In some embodiments, the thickness is no greater than 200, 150, 100, 75, or 60 microns. The basis weight typically ranges from 2 to 10, 15, 20, 25 or 30 $mg/cm^2$.

The fibrinogen concentration of the sheet article is the same as the (e.g. dehydrated) fibrinogen hydrogel as previously described.

Figure 3:
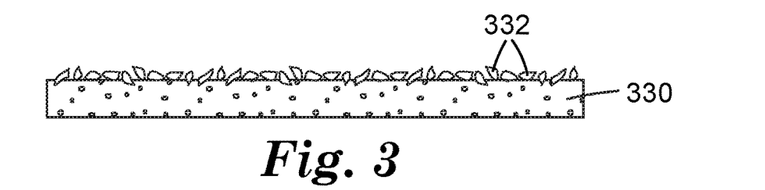
FIG. 3 is a schematic cross-section of an illustrative embodiment fibrinogen article suitable for a wound dressing comprising a sheet of foam and fibrinogen particles.

FIG. 3 illustrates another embodiment of a fibrinogen article, suitable for use as a wound dressing. The fibrinogen article includes a carrier sheet of fibrinogen-containing foam 230 or foam lacking fibrinogen 310. The foam 230 or 310 further comprises a plurality of fibrinogen particles 332 comprising the (e.g. dehydrated) fibrinogen hydrogel disposed on and/or within the pores of the wound-facing surface of the foam. The particles may be fibrinogen microbeads, fibrinogen microcarriers, or fibrinogen powder as previously described.

Figure 4:
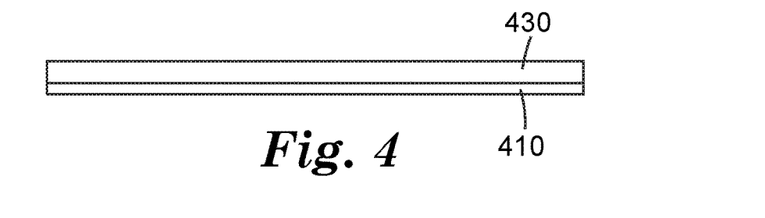
FIG. 4 is a schematic cross-section of an illustrative embodiment of a fibrinogen article suitable for a wound dressing comprising a fibrinogen-containing layer and a carrier layer.

Each of the embodiments of FIGS. 1-3 may further comprise a carrier layer disposed on a major surface of the fibrinogen-containing sheet article. A carrier layer is typically disposed on the opposing major surface as the wound-facing surface. For example, FIG. 4 illustrates an embodiment of a fibrinogen article, suitable for use as a wound dressing. The fibrinogen article includes a sheet 430 comprising or consisting of the (e.g. dehydrated) fibrinogen gel composition (e.g. 130, 230, or 310 together with 332) and a carrier layer 410.

In some embodiments, carrier layer 410 is a release liner. The release liner carrier may be disposed on the opposing major surface of both major surfaces (not shown) such that the fibrinogen-containing sheet is between the release liner layers.

Various release liners are known such as those made of (e.g. kraft) papers, polyolefin films such as polyethylene and polypropylene, or polyester. The films are preferably coated with release agents such as fluorochemicals or silicones. For example, U.S. Pat. No. 4,472,480 describes low surface energy perfluorochemical liners. Examples of commercially available silicone coated release papers are POLYSLIK™, silicone release papers available from Rexam Release (Bedford Park, Ill.) and silicone release papers supplied by LOPAREX (Willowbrook, Ill.). Other non-limiting examples of such release liners commercially available include siliconized polyethylene terephthalate films commercially available from H. P. Smith Co. and fluoropolymer coated polyester films commercially available from 3M under the brand "ScotchPak™" release liners.

In other embodiments, the carrier layer 410 may comprise a variety of other (e.g. flexible and/or conformable) materials such as polymeric films and foams as well as various nonwoven and woven fibrous materials, such as gauze. In some embodiments, the carrier layer is absorbent, such as an absorbent foam. In other embodiments, the carrier layer is non-absorbent, such as a polymeric film.

Figure 5:
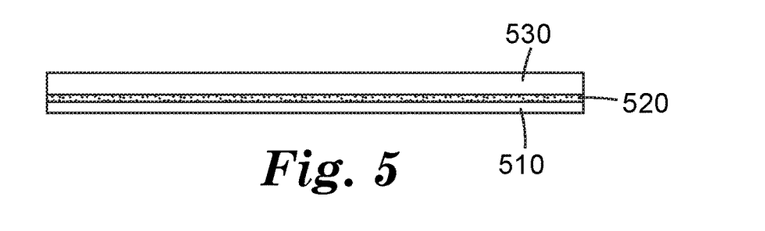
FIG. 5 is a schematic cross-section of an illustrative embodiment of a fibrinogen article suitable for a wound dressing comprising a fibrinogen-containing layer, a carrier layer, and a (e.g. pressure sensitive) adhesive.

In some embodiments, the fibrinogen article, suitable for use as a wound dressing, further comprises a (e.g. pressure sensitive) adhesive. The adhesive may be utilized to bond the fibrinogen composition (e.g. sheet or particles) to the carrier layer. For example, FIG. 5 illustrates a fibrinogen-containing sheet 530 comprising or consisting of the (e.g. dehydrated) fibrinogen gel composition and a carrier layer 510 such as a polymeric film or foam. A (e.g. pressure sensitive) adhesive layer 520 bonds the fibrinogen-containing sheet 530 to the carrier layer 510. Fibrinogen-containing sheet 530 may be 130, 230, or 310 together with 332 as previously described with reference to FIGS. 1-3.

Figure 6:
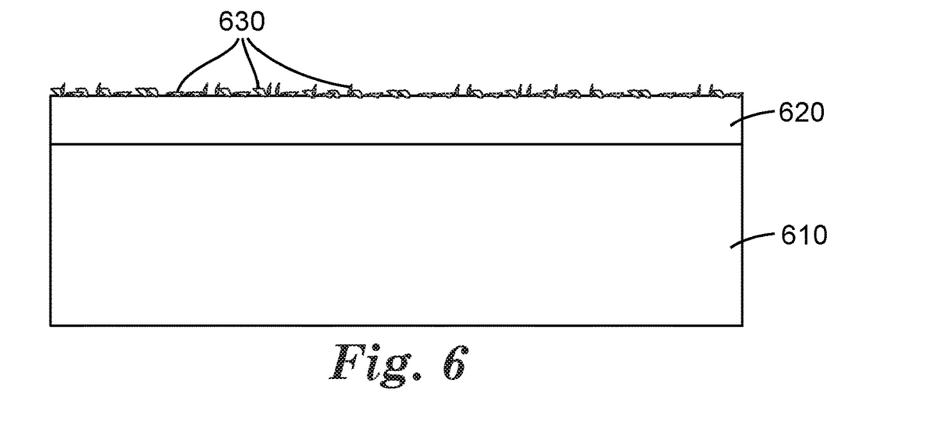
FIG. 6 is a schematic cross-section of an illustrative embodiment of a fibrinogen article suitable for a wound dressing comprising a carrier layer, a (e.g. pressure sensitive) adhesive; and (e.g. dehydrated) fibrinogen hydrogel containing particles.

In some embodiments, the fibrinogen article comprises a skin contacting adhesive for bonding the article to the skin (e.g. of a mammal such as a human). Such skin contact adhesive is typically a pressure sensitive adhesive. In some embodiments, the pressure sensitive adhesive may bond fibrinogen particles to a carrier layer. The fibrinogen particles and optionally portions of the pressure sensitive adhesive may contact the wound during use. For example, FIG. 6 illustrates another embodiment of a fibrinogen article, suitable for use as a wound dressing. The fibrinogen article includes a carrier layer 610 that may be a release liner, a polymeric film or foam, etc., a pressure sensitive adhesive layer 620 is disposed on the carrier layer 610 and fibrinogen particles 630, as described herein, are disposed on and optionally at least partially embedded in the pressure sensitive adhesive layer. The skin contact adhesive is typically covered by a removable release liner until use.

Figure 7:
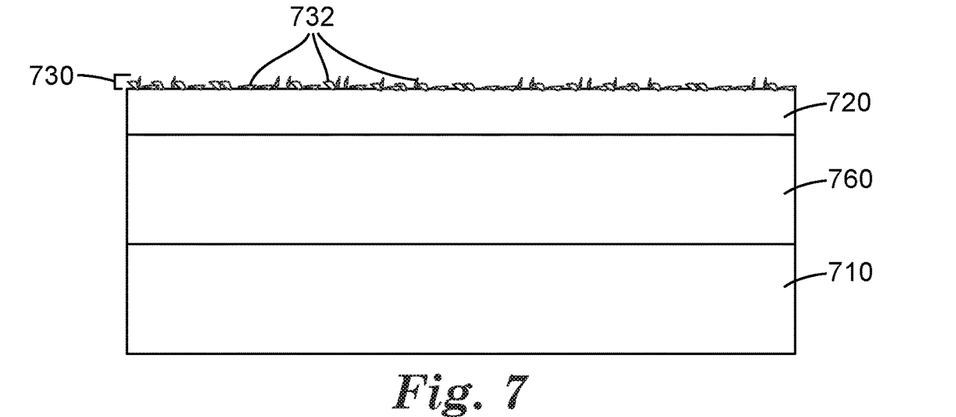
FIG. 7 is a schematic cross-section of an illustrative embodiment of a fibrinogen article suitable for a wound dressing comprising a carrier layer, an absorbent, a (e.g. pressure sensitive) adhesive; and fibrinogen-containing layer.

In some embodiments, the wound dressing comprises an absorbent layer. The absorbent layer is typically disposed between the wound facing fibrinogen-containing layer and a polymeric film. For example, FIG. 7 illustrates another embodiment of a fibrinogen article, suitable for use as a wound dressing. The fibrinogen article includes a carrier layer 710 that may be a (e.g. flexible) polymeric film. An absorbent layer 760 such as a polymeric foam is disposed on the carrier layer 710. A pressure sensitive adhesive ("PSA") layer 720 is disposed on the absorbent layer 760 and a fibrinogen-containing layer 730 is disposed on the pressure sensitive adhesive layer 720. The fibrinogen-containing layer may be any of the previously described fibrinogen-containing layers such as sheet 130, foam sheet 230, or fibrinogen particles 332.

Figure 8:
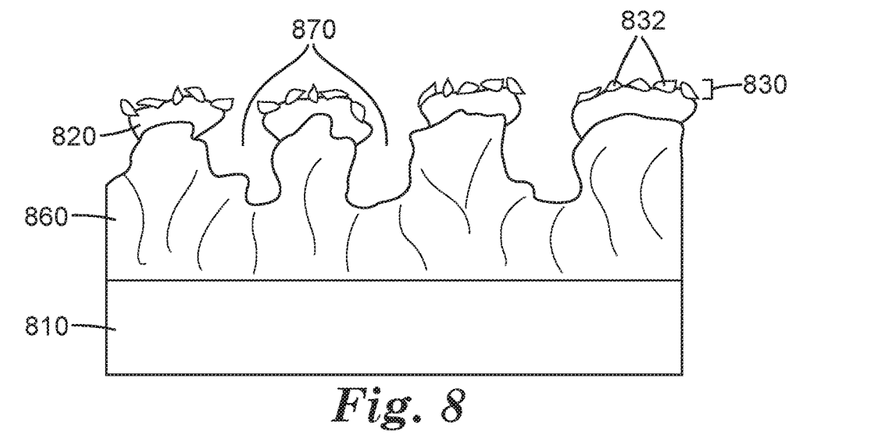
FIG. 8 is a schematic cross-section of an illustrative carrier layer and fibrinogen-containing layer comprising a discontinuous skin adhesive and (e.g. dehydrated) fibrinogen hydrogel containing particles.

As shown in FIG. 8, an adhesive layer 820 may be provided in a discontinuous form, at external surfaces of absorbent layer 860, to allow penetration of wound fluids and cellular debris into the absorbent foam layer. In some embodiments, the adhesive is a pressure sensitive adhesive. In other embodiments, the adhesive is not a pressure sensitive adhesive. The fibrinogen particles 832 in fibrinogen layer 830 are thus displayed in correspondingly discontinuous manner at the outer surface of absorbent layer 860. The adhesive layer 820 may extend into and through a portion of absorbent layer 860. Portions of the adhesive layer 820 can extend over open cells 870, although it is desirable at least a portion (e.g., at least 10%, or at least 50%) of the cells at the external surface of absorbent layer 860 are not closed with the adhesive. Absorbent layer 860 can be adhered to (e.g. flexible) film layer 810 by a suitable adhesive layer. In this embodiment, the fibrinogen particles may be fibrinogen microbeads, fibrinogen microcarriers, or fibrinogen powder as previously described. In one embodiment, a solution of pressure-sensitive adhesive can be sprayed onto a carrier layer such as an open cell foam at a suitable coating weight (e.g., 5-15 mg/cm$^2$) and after drying the PSA layer, fibrinogen particles can be coated onto the adhesive coated surface. The fibrinogen particles can thus be deposited on an exterior surface of the foam with some additional loading into pores of the open cell foam. Such a fibrinogen particles/PSA/absorbent foam construct has been observed to readily absorb moisture. This approach is also suitable for incorporating fibrinogen particles on elastomeric carrier layers.

In another embodiment, a fibrinogen particle layer can be disposed on a pressure-sensitive adhesive layer, which in turn is disposed on a flexible, porous, non-woven backing layer. The non-woven backing layer can be reinforced with filaments (e.g., polyester filaments) for added strength. An example of such a non-woven-backing coated with a (hypoallergenic) pressure-sensitive adhesive can include sterile skin closure strips (e.g., STERI-STRIPS, available from 3M Co., St. Paul, Minn.). The addition of a fibrinogen (e.g. particle) layer to such sterile skin closure strips can have beneficial effects, for example, in scar management at incision or wound sites (i.e., to reduce scar formation).

Figure 9:
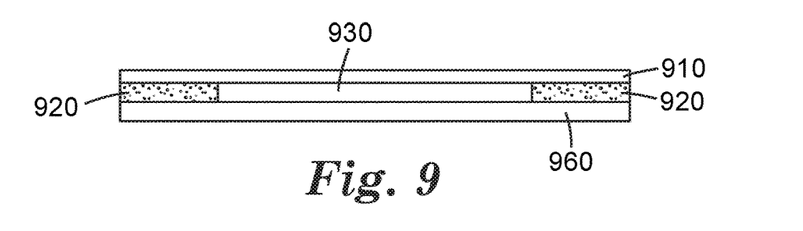
FIG. 9 is a schematic cross-section of another illustrative embodiment of a fibrinogen article suitable for a wound dressing comprising a carrier layer, fibrinogen-containing layer, skin contact pressure sensitive adhesive, and release liner.
Figure 10:
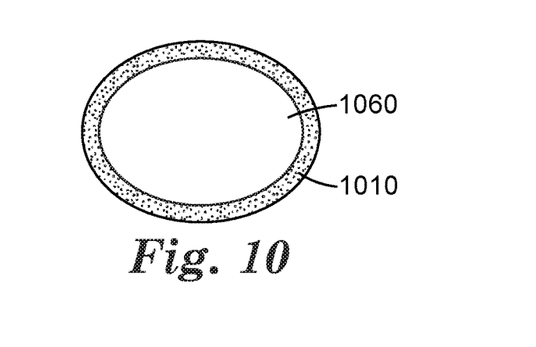
FIG. 10 is a top plan view of the wound-facing surface of the article of FIG. 10.
Figure 11:
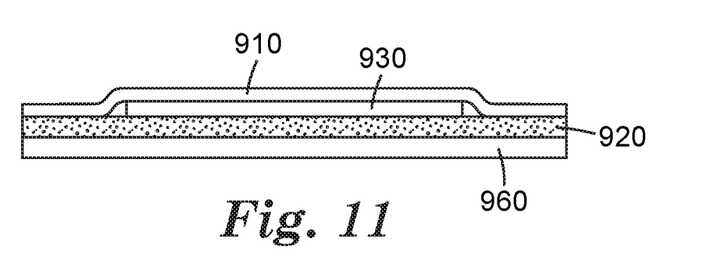
FIG. 11 is a schematic cross-section of another illustrative embodiment of a fibrinogen article suitable for a wound dressing comprising a carrier layer, fibrinogen-containing layer, skin contact pressure sensitive adhesive, and release liner.

In other embodiments, a skin contact adhesive is located at the periphery of the article such that the adhesive typically contacts the skin outside of the wound such as near the periphery of a wound. The skin contact adhesive is typically covered by a removable release liner until use. For example, FIG. 9 illustrates another embodiment of a fibrinogen article, suitable for use as a wound dressing. The fibrinogen article includes a carrier layer 960 that is typically a polymeric film, a pressure sensitive skin adhesive 920 is disposed at peripheral regions of the film, a fibrinogen sheet 930 is disposed on film 960 in the middle region between adhesive 920, a removable release liner 910 is disposed on the fibrinogen sheet and the adhesive. Alternatively, the release liner may be disposed only upon the adhesive as depicted in FIG. 10. In FIG. 11, the (e.g same) skin contact adhesive is utilized to bond the fibrinogen sheet to the polymeric film carrier layer 960.

In some embodiments, the carrier layer of the wound dressing is a flexible film layer, (also referred to as a "backing" layer), typically includes a liquid impervious, moisture vapor permeable (e.g. breathable) polymeric film. The liquid impervious, moisture vapor permeable polymeric film is a conformable organic polymeric material that preferably retains its structural integrity in a moist environment. Herein, "conformable" films are those that conform to a surface, even upon movement of the surface, as with the surface of a body part. As such, when the flexible film layer is applied to an anatomical feature, it conforms to the surface even when the surface is moved. The preferred flexible film layer is also conformable to animal anatomical joints. When the joint is flexed and returned to its unflexed position, the flexible film layer stretches enough to accommodate the flexion of the joint, but is resilient enough to continue to conform to the joint when the joint is returned to its unflexed condition. A description of this characteristic of flexible film layers preferred for use in wound dressings of the present disclosure can be found, for example, in U.S. Pat. No. 5,088,483 (Heineke) and U.S. Pat. No. 5,160,315 (Heineke).

Suitable films have a composition and thickness that allow for the passage of moisture vapor through them. The film aids in the regulation of water vapor loss from the wound area beneath the dressing. The film also acts as a barrier to both bacteria and to liquid water or other liquids.

The moisture vapor permeable polymeric films for use as flexible film layers in the present disclosure can be of a wide range of thicknesses. In some embodiments, the flexible film layers have a thickness of at least 10 or 12 microns ranging up to 250 microns. In some embodiments, the flexible film layer has a thickness no greater than 75 microns.

Moisture vapor transmission rate ("MVTR") properties of a wound dressing article are important to allow the wound under the wound dressing to heal in moist conditions without causing the skin surrounding the wound to become macerated, and to facilitate optimum wear time and ease of removal.

A dry MVTR (or upright MVTR) of wound dressings or various components thereof, including the flexible film layer, can be measured by ASTM E-96-80 (American Society of Testing Materials) at 40° C. and 20% relative humidity using an upright cup method. Wet MVTR (or inverted MVTR) can be measured by the same method except that the sample jars are inverted so the water is in direct contact with the test sample.

In some embodiments, the film has a dry MVTR that is less than the wet MVTR of the film. For example, the film may have a dry MVTR of at least 300 g/m$^2$/24 hours and a wet MVTR of at least 500, 1000, 2000 or 3000 g/m$^2$/24 hours. In some embodiments, the film has a wet MVTR greater 10,000 g/m$^2$/24 hours or 15,000 g/m$^2$/24 hours.

Examples of suitable materials for the liquid-impervious, moisture-vapor permeable polymeric films of the flexible film layer include synthetic organic polymers including, but not limited to: polyurethanes commercially available from B.F. Goodrich, Cleveland, Ohio, under the trade designation ESTANE, including ESTANE 58237 and ESTANE 58245; polyetheramide block copolymers commercially available from Elf Atochem, Philadelphia, Pa., under the trade designation PEBAX, including PEBAX MV 1074; polyetherester block copolymers commercially available from DuPont, Wilmington, Del., under the trade designation HYTREL; and thermoplastic elastomers commercially available from DSM Engineering Plastics, Evansville, Ind., under the trade designation ARNITEL VT. The polymeric films can be made of one or more types of monomers (e.g., copolymers) or mixtures (e.g., blends) of polymers. Preferred materials are thermoplastic polymers, e.g., polymers that soften when exposed to heat and return to their original condition when cooled. A particularly preferred material is a thermoplastic polyurethane.

Flexible films of the wound dressing articles of the present disclosure can also include other breathable materials including, for example, nonwoven, woven, and knit webs, porous films (e.g., provided by perforations or microporous structure), foams, paper, or other known flexible films. A preferred flexible film includes a combination of a liquid-impervious, moisture-vapor permeable polymeric film and a moisture-vapor permeable nonwoven web that can, among other advantages, impart enhanced structural integrity and improved aesthetics to the dressings. These layers of film and web may or may not be coextensive. A preferred such nonwoven web is a melt processed polyurethane (such as that available under the trade designation MORTHANE PS-440 from Morton International, Seabrook, N.H.), or hydroentangled nonwoven polyester or rayon-polyester webs (such as those available under the trade designation SONTARA 8010 or SONTARA 8411 from DuPont, Wilmington, Del.).

In some embodiments, flexible film layer is translucent, semi-transparent, or transparent, although this is not a requirement. Some examples of wound dressings that include a transparent or translucent flexible film layer are available under the trade designation TEGADERM, available from 3M Co., St. Paul, Minn.

A low adhesion coating (low adhesion backsize or LAB) can be provided on the flexible film layer on the side that may come into contact with an optional support layer. The low adhesion coating reduces the need to change the dressing due to unwanted dressing removal when other tapes or devices are placed on the dressing and removed, and reduces the surface friction of the dressing on linen or other fabrics, thereby offering additional protection against the accidental removal of dressing. A description of a low adhesion coating material suitable for use with a wound dressing article of the present disclosure can be found in U.S. Pat. No. 5,531,855 (Heineke) and U.S. Pat. No. 6,264,976 (Heineke).

In some embodiments, the wound dressing comprises an absorbent layer. In some embodiments, the absorbent layer can include an absorbent foam layer, or at least a portion of an absorbent foam layer disposed on the flexible film layer. A suitable foam layer can include, for example, an open cell foam selected from among the open cell foams described in U.S. Pat. No. 6,548,727 (Swenson). Suitable open cell foams preferably have an average cell size (typically, the longest dimension of a cell, such as the diameter) of at least about 30 microns, more preferably at least about 50 microns, and preferably no greater than about 800 microns, more preferably no greater than about 500 microns, as measured by scanning electron microscopy (SEM) or light microscopy. Such open cell foams when used in wound dressings of the present disclosure allow transport of fluid and cellular debris into and within the foam. In some embodiments, the foam includes a synthetic polymer that is adapted to form a conformable open cell foam that absorbs wound exudate. Examples of suitable materials for the absorbent, substantially nonswellable foams include synthetic organic polymers including, but not limited to: polyurethanes, carboxylated butadiene-styrene rubbers, polyesters, and polyacrylates. The polymeric foams can be made of one or more types of monomers (e.g., copolymers) or mixtures (e.g., blends) of polymers. Preferred foam materials are polyurethanes. A particularly preferred foam is a polyurethane, available under the trade designation POLYCRIL 400 from Fulflex, Inc., Middleton, R.I. In other embodiments, the foam comprises or consists of the (e.g. dehydrated) fibrinogen hydrogel.

In another embodiment, the absorbent layer may comprise a non-woven or a fiber material. In an embodiment where the absorbent material includes a fiber material, the fiber material can be a sheath-core fiber having a central core of absorbent fiber and a sheath comprising pressure-sensitive adhesive.

In some embodiments, the absorbent layer may extend around a peripheral region of the wound dressing, to absorb fluids that might otherwise accumulate on skin and result in undesirable skin degradation (e.g., maceration). In such embodiments, an absorbent layer would not need to be included in a more central region of the wound dressing (e.g., the portion of the wound dressing that is in contact with the wound, or positioned over the wound).

The fibrinogen article, suitable for use as a wound dressing, may comprise various adhesives to bond layers of the article. The fibrinogen article may also comprises various PSAs for bonding the article to skin. The (e.g. PSA) adhesive layer can be continuous, discontinuous, pattern coated, or melt-blown, for example.

PSAs typically have a storage modulus (G') of less than $1 \times 10^6$ dynes/cm$^2$ at 25° C. and a frequency of 1 hertz. In some embodiments, the PSA has storage modulus (G') of less than 9, 8, 7, 6, 5, 4, or $3 \times 10^5$ dynes/cm$^2$ at 25° C. and a frequency of 1 hertz.

Examples of PSAs include rubber based adhesives (e.g., tackified natural rubbers, synthetic rubbers, and styrene block copolymers), acrylics (e.g., polymerized (meth)acrylates), poly(alpha-olefins), polyurethanes, and silicones. Amine containing polymers can also be used which have amine groups in the backbone, pendant thereof, or combinations thereof. A suitable example includes a poly(ethyleneimine).

Useful adhesives can be any of those that are compatible with skin and useful for wound dressings, such as those disclosed in U.S. Pat. Nos. Re. 24,906 (Ulrich), U.S. Pat. No. 5,849,325 (Heinecke et al.), and U.S. Pat. No. 4,871,812 (Lucast et. al.) (water-based and solvent-based adhesives); U.S. Pat. No. 4,833,179 (Young et al.) (hot-melt adhesives); U.S. Pat. No. 5,908,693 (Delgado et al.) (microsphere adhesives); U.S. Pat. Nos. 6,171,985 and 6,083,856 (both to Joseph et al.) (low trauma fibrous adhesives); and, U.S. Pat. No. 6,198,016 (Lucast et al.), U.S. Pat. No. 6,518,343 (Lucast et al.), and U.S. Pat. No. 6,441,082 (Gieselman) (wet-skin adhesives). Inclusion of medicaments or antimicrobial agents in the adhesive is also contemplated, as described in U.S. Pat. No. 4,310,509 (Berglund) and U.S. Pat. No. 4,323,557 (Rosso).

The adhesive can be coated on the carrier layer by a variety of processes, including, direct coating, lamination, and hot lamination. In some embodiments, the adhesive may be coated as a microstructured adhesive layer.

Silicone and acrylic based pressure sensitive adhesives are most commonly utilized for adhering to the skin, whereas the other classes of adhesives can be utilized to bond layers of the fibrinogen article suitable for use as a wound dressing.

Silicone PSAs include two major components, a polymer or gum, and a tackifying resin. The polymer is typically a high molecular weight polydimethylsiloxane or polydimethyldiphenyl-siloxane, that contains residual silanol functionality (SiOH) on the ends of the polymer chain, or a block copolymer including polydiorganosiloxane soft segments and urea terminated hard segments. The tackifying resin is generally a three-dimensional silicate structure that is endcapped with trimethylsiloxy groups ($OSiMe_3$) and also contains some residual silanol functionality. Examples of tackifying resins include SR 545, from General Electric Co., Silicone Resins Division, Waterford, N.Y., and MQD-32-2 from Shin-Etsu Silicones of America, Inc., Torrance, Calif. Manufacture of typical silicone PSAs is described in U.S. Pat. No. 2,736,721 (Dexter). Manufacture of silicone urea block copolymer PSA is described in U.S. Pat. No. 5,214,119 (Leir et al.).

In some embodiments, the silicone adhesive may be characterized as gentle to skin such as described in US2011/0212325, US2011/0206924, US2011/0206923, US2013/0040073, U.S. Pat. Nos. 7,407,709 and 787,268.

In some embodiments, the PSAs is an acrylic PSAs typically having a glass transition temperature of about −20° C. or less and may include from 100 to 60 weight percent of a C4-C12 alkyl ester component such as, for example, various (meth)acrylate monomers including isooctyl acrylate, 2-ethyl-hexyl acrylate and n-butyl acrylate and from 0 to 40 weight percent of a polar component such as, for example, acrylic acid, methacrylic acid, ethylene, vinyl acetate, N-vinyl pyrrolidone and styrene macromer.

Suitable acidic monomers for preparing (meth)acrylic PSAs include those containing carboxylic acid functionality such as acrylic acid, methacrylic acid, itaconic acid, and the like; those containing sulfonic acid functionality such as 2-sulfoethyl methacrylate; and those containing phosphonic acid functionality. Preferred acidic monomers include acrylic acid and methacrylic acid.

Additional useful acidic monomers include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, B-carboxyethyl acrylate, 2-sulfoethyl methacrylate, styrene sulfonic acid, 2-acrylamido-2-methylpropane sulfonic acid, vinyl phosphonic acid, and the like, and mixtures thereof.

Due to their availability, acidic monomers of the present invention are typically the ethylenically unsaturated carboxylic acids. When even stronger acids are desired, acidic monomers include the ethylenically unsaturated sulfonic acids and ethylenically unsaturated phosphonic acids. Sulfonic and phosphonic acids generally provide a stronger interaction with a basic polymer. This stronger interaction can lead to greater improvements in cohesive strength, as well as higher temperature resistance and solvent resistance of the adhesive.

Suitable basic monomers for preparing (meth)acrylic PSAs include those containing amine functionality such as vinyl pyridine, N,N-diethylaminoethyl methacrylate, N,N-dimethylamino-ethyl methacrylate, N,N-diethylaminoethyl acrylate, N,N-dimethylaminoethyl acrylate, and N-t-butylaminoethyl methacrylate. Preferred basic monomers include N,N-dimethylaminoethyl methacrylate, and N,N-dimethylaminoethyl acrylate.

The (meth)acrylic PSAs may be self-tacky or tackified. Useful tackifiers for (meth)acrylics are rosin esters such as that available under the trade name FORAL 85 from Hercules, Inc., aromatic resins such as that available under the trade name PICCOTEX LC-55WK from Hercules, Inc., aliphatic resins such as that available under the trade name PICCOTAC 95 from Hercules, Inc., and terpene resins such as that available under the trade names PICCOLYTE A-115 and ZONAREZ B-100 from Arizona Chemical Co. Other materials can be added for special purposes, including hydrogenated butyl rubber, pigments, and curing agents to vulcanize the adhesive partially. Examples of acid-modified tackifiers include acid-modified polyhydric alcohol rosin ester tackifiers as described in U.S. Pat. No. 5,120,781 (Johnson).

In certain embodiments, the (e.g. acrylic) PSA comprises polymerized unit of a poly(alkylene oxide) such as poly (ethylene oxide) and/or poly(propylene oxide). The PSA typically comprises at least 5, 10 or 15 wt.-% and typically no greater than about 30 wt.-% of polymerized poly(alkylene oxide).

In some embodiments, a poly(alkylene oxide) copolymer is blended with a (meth)acrylic copolymer. Examples of useful poly(alkylene oxide) copolymers include, but are not limited to, those poly(alkylene oxide) copolymers available under the trade designations TETRONIC (tetrafunctional block copolymers derived from sequential addition of propylene oxide and ethylene oxide to ethylene diamine with hydrophilic endblocks) and TETRONIC R (tetrafunctional block copolymers derived from sequential addition of propylene oxide and ethylene oxide to ethylene diamine with hydrophobic endblocks) copolymers available from BASF, Mt. Olive, N.J.; PLURONIC (triblock copolymers with poly(ethylene oxide) end blocks and poly(propylene oxide) midblock) and PLURONIC R (triblock copolymers with poly(propylene oxide) endblocks and poly(ethylene oxide) midblock) copolymers available from BASF; UCON Fluids (random copolymers of ethylene oxide and propylene oxide) available from Union Carbide, Danbury, Conn. Various combinations of poly(alkylene oxide) copolymers can also be used. Preferred nonreactive hydrophilic polymer components are block copolymers of polyethylene glycol and propylene glycol available from BASF, Germany under the trade name PLURONIC.

In other embodiments, a poly(alkylene oxide) monomer having a copolymerizable (e.g. vinyl) group is included during the polymerization of the acrylic polymer. Commercially available monomers include 2-(2-ethoxyethoxy)ethyl acrylate which is available under the trade designation "SR-256" from Sartomer Company, West Chester, Pa.; the methoxy poly(ethylene oxide) acrylate which is available under the trade designation "No. 8816" from Monomer-Polymer & Dajac Laboratories, Inc., Trevose, Pa.; the methoxy poly(ethylene oxide) methacrylates of 200 Daltons, 400 Daltons, and 1000 Daltons which are available under the trade designations "No. 16664", "No. 16665" and "No. 16666", respectively, from Polysciences, Inc., Warrington, Pa.; and the hydroxy poly(ethylene oxide) methacrylate which is available under the trade designation "No. 16712" from Polysciences, Inc., Warrington, Pa.

Examples of acrylic adhesive compositions include a 97:3 iso-octyl acrylate:acrylamide copolymer 65:15:20 2-ethylhexylacrylate:acrylic acid:copolymer blended with a nonreactive polyakylene oxide copolymer under the trade designation PLURONIC. Other suitable examples include a 90:10 iso-octyl acrylate:acrylic acid copolymer, a 70:15:15 isooctyl acrylate:ethylene oxide acrylate:acrylic acid terpolymer, and a 25:69:6 2-ethylhexylacrylate:butyl acrylate:acrylic acid terpolymer. Additional useful adhesives are described in U.S. Pat. Nos. 3,389,827, 4,112,213, 4,310,509, and 4,323,557.

Inclusion of medicaments or antimicrobial agents in the adhesive is also contemplated, as described in U.S. Pat. Nos. 4,310,509 and 4,323,557.

Pressure sensitive adhesives for wound dressings preferably transmit moisture vapor at a rate greater to or equal to that of human skin. While such a characteristic can be achieved through the selection of an appropriate adhesive, it is also contemplated in the present disclosure that other methods of achieving a high relative rate of moisture vapor transmission may be used, such as pattern coating the adhesive on the backing, as described in U.S. Pat. No. 4,595,001 (Potter et al.).

A composite of flexible film layer coated with pressure-sensitive adhesive layer preferably has a moisture vapor transmission rate of at least 300 g/m$^2$/24 hrs/37° C./100%-10% relative humidity ("RH"), more preferably at least 700 g/m$^2$/24 hrs/37° C./100%-10% RH, and even more preferably at least 2000 g/m$^2$/24 hrs/37° C./100%-10% RH using the inverted cup method as described in U.S. Pat. No. 4,595,001.

In some embodiment, the method of making a fibrinogen article generally comprises providing a (e.g. dehydrated) fibrinogen composition and disposing the fibrinogen composition on or within a carrier. In some embodiments, the carrier is a carrier layer such as a release liner, a polymeric film or foam, or a nonwoven or woven fibrous material. When the fibrinogen composition is in a particle form, the methods of making the wound dressing can include distributing fibrinogen particles onto a (e.g. pressure-sensitive) adhesive layer disposed on a carrier. Alternatively, the fibrinogen particles can be suspended in a liquid (e.g., an inert, volatile fluorinated liquid) and spray dried in a dehydrated form onto the surface of a (e.g. pressure-sensitive adhesive) layer disposed on a carrier layer. Examples of suitable wound dressings that include a pressure-sensitive adhesive layer disposed on flexible film layer include TEGADERM wound dressings (e.g., TEGADERM 1626) available from 3M Co., St. Paul, Minn. In one embodiment, the fibrinogen-containing layer (e.g. sheet or particles) are applied to the surface of a pressure-sensitive adhesive layer of a TEGADERM wound dressing.

A wound dressing article of the present description is typically provided in a package format (i.e., positioned in a sealed package). The interior of the sealed package is typically sterile. Examples of wound dressing packages suitable for use with the wound dressings and methods of this disclosure include, for example, polymeric packages and foil packages. A wide variety of polymeric materials may be used to make non-porous packages suitable for use with the wound dressings. The packaging material may be, for example, polyethylene, polypropylene, copolymers of ethylene and propylene, polybutadiene, ethylene-vinyl acetate, ethylene-acrylic acid, or ionomeric films. Suitable foil packages can include aluminum foil packages. In some embodiments, the packaging material may be used as sheets of material which are placed above and below the wound dressing and then sealed on four sides to generate the package. In other embodiments, a pre-made pouch is utilized which has 3 sides already sealed. After the wound dressing article is placed within the pouch the fourth side is sealed to form the package. Sealing of the package can be achieved by heat sealing (i.e. by the application of heat and pressure to form a seal) or the use of adhesive sealants can be used to seal the packages (for example pressure sensitive adhesive sealants or cold seal sealants). Typically, heat sealing is used. Additionally, packaging systems can be used which include placing the wound dressing in a porous package that is then placed in a non-porous package, such as a foil package. The foil package prevents moisture loss prior to use and the porous package permits easy handling during use.

An advantage of a wound dressing article of the present disclosure is that it can be sterilized by a terminal sterilization process that includes exposure to ethylene oxide or, advantageously, gamma-irradiation. This irradiation can be carried out whether or not the wound dressing article is contained within a package. The exposure times and levels of radiation doses applied to the wound dressings to achieve sterilization can vary based upon a variety of factors, including the gamma equipment used as well as the inherent bioburden levels present in the wound dressing. Typically, to achieve sterilization of a wound dressing, a Sterility Assurance Level (SAL) of $10^{-6}$ is required. This SAL level is typically achieved by exposing the wound dressing to a minimum cumulative gamma irradiation dose. Depending on the bioburden levels in an unsterilized dressing and the size of the dressing, the minimum cumulative dose can range from about 10 kGy to about 35 kGy. Typically the minimum cumulative dose is about 15 to 30 kGy. In other embodiment, a dosage of about 50 to 60 kGy may be utilized. The required gamma radiation dose to achieve sterility can be done in a single pass or multiple passes through the gamma irradiation sterilizer. For example, exposing the wound dressing to 5 sterilization cycles using a dose of 5 kGy per cycle would be similar to exposing the wound dressing to one dose of 25 kGy of gamma irradiation. Due to labor and time constraints, it is generally desirable to minimize the number of passes that a wound dressing experiences through the gamma irradiation sterilizer. Typically, it is desirable that the number of passes through the sterilizer be five or less, and it may be even more desirable for the number of passes to be two or less. Exposure time may be viewed as the time a sample to be sterilized is exposed to the gamma radiation. Typically the exposure time is on the order of hours.

Gamma radiation is a suitable method to sterilize the wound dressings of this disclosure. Exposure of the wound dressings of this disclosure to a suitable level gamma irradiation does not produce a comparable loss of re-epithelialization performance.

The ability to use terminal sterilization can provide an advantage over other forms of wound dressings that include, for example, a liquid. Without being bound by theory, aqueous solutions or suspensions of proteins such as fibrinogen and thrombin can be expected to undergo inter-chain crosslinking during terminal sterilization that involves gamma-irradiation. In a dry format, a protein will often undergo chain scission (i.e., degradation) and thereby lose enzymatic activity. Thus, gamma-irradiation of the reagents for a polymerization (e.g., fibrinogen and/or thrombin) may result in crosslinking and/or chain scission of the separate reagents, and thus no reaction (or no polymerization) to form fibrin. Depending on the level of gamma-irradiation, fibrin may also undergo some chain scission, although even with low levels of degradation, the gamma-irradiated fibrin still can be recognized by cells to obtain the desired re-epithelialization effect.

The (e.g. dehydrated) fibrinogen hydrogel in its various physical forms can be utilized for the treatment of wounds. Thus, in another embodiment, a method of treatment of a (e.g. mammal or human) wound is described providing the fibrinogen composition as described herein or a wound dressing comprising the described fibrinogen composition and providing the fibrinogen composition proximate a wound. In typical embodiments, the fibrinogen-containing layer (e.g. sheet, foam, particles) is in direct contact with at least a portion or portions of the wound. Alternatively, it is surmised that the fibrinogen-containing layer may be in close proximity, yet not in direct contact. For example, it is contemplated that an absorbent porous carrier layer, such as a gauze, may comprise the fibrinogen-containing layer on the opposing surface as the wound facing surface. During use fluids of the wound penetrate through the absorbent porous carrier layer thereby degrading the fibrinogen-containing layer.

The fibrinogen composition has been shown to increase the rate of re-epithelialization in both in-vivo porcine studies and in-vitro studies using human primary isolated cells. In some embodiments, the re-epithelialization was 2 times faster than the control (same dressing without (e.g. dehydrated) fibrinogen hydrogel).

The dehydrated fibrinogen composition was also been found to affect the formation of pro-healing and anti-healing biomarkers such as growth factors, proteases, cytokines as commonly known in the art. (See Murphy, K. (2012). *Janeway's Immunobiology* (E. Lawrence Ed. 8th ed.): Garland science). In some embodiments, the formation of VEGF—vascular endothelial growth factor was at least 1, 2, 3, or 4 times greater than the control. In some embodiments, the EGF—epidermal growth factor was as least 1 or 2 times greater than the control. In some embodiments, the formation of matrix metalloproteinase—MMP1 and/or MMP8— was at least 1, 2, 3, 4, 5, 6, 7, 8, or 9 times greater than the control. In some embodiments, the formation of matrix metalloproteinase—MMP9—was at least 10, 20, 30, 40, 50, 60, 70, or 80 times greater than the control. In some embodiments, the formation of TIMP1—tissue inhibitor of metalloproteinase was at least 1, 2, 3, or 4 times greater than the control. Prohealing markers IL-4, IL-6, IL-10, EGF, FGF-basic were the same as the control, indicating no effect. Further, anti-healing biomarkers TNF-alpha, IL1-alpha, IL-1beta, IL-2 were all below the detection limit of the assay, indicating a low pro-inflammatory profile.

All patents and patent applications cites herein are incorporated by reference. Other modifications and variations to the present disclosure may be practiced by those of ordinary skill in the art, without departing from the spirit and scope of the present disclosure. It is understood that aspects of the various embodiments may be interchanged in whole or part or combined with other aspects of the various embodiments. The preceding description, given in order to enable one of ordinary skill in the art to practice the claimed disclosure, is not to be construed as limiting the scope of the disclosure, which is defined by the claims and all equivalents thereto.

EXAMPLES

Unless otherwise noted, all parts, percentages, ratios, etc. in the Examples and the rest of the specification are by weight. "Weight percent" is in some places abbreviated as "wt.-%".

Materials $CaCl_2$, NaCl were obtained from SIGMA-Aldrich (Milwaukee, Wis.). Other materials are listed as used in the Examples below.

Preparatory Example P1. Preparation of Fibrinogen Solution

Preparatory Example P1-A, a fibrinogen solution in water, was prepared by dissolving 5.1 grams fibrinogen powder (Bovogen Biologicals, Australia) in 24.9 grams of deionized water (Honeywell International Inc, USA) at 40° C. The fibrinogen solutions were also prepared at different concentrations. Fibrinogen concentration is important for obtaining a smooth de-natured sheet. For a coat-able solution, a minimum viscosity of 200 cps is preferred. The fibrinogen concentrations, along with subsequent viscosities, of examples P1-A through P1-H are listed below in TABLE 1. It was not possible to dissolve fibrinogen at concentrations at or above 18% w/w due to the high viscosity that immobilized the system.

TABLE 1

FIBRINOGEN/WATER SOLUTIONS AT VARIOUS CONCENTRATIONS

| | EXAMPLE | | | | | | | |
|---|---|---|---|---|---|---|---|---|
| | P1-A | P1-B | P1-C | P1-D | P1-E | P1-F | P1-G | P1-H |
| Fibrinogen (g) | 5.1 | 12 | 12.8 | 13.2 | 13.6 | 14 | 14.4 | 15.2 |
| Deionized water (g) | 24.9 | 68 | 67.2 | 66.8 | 66.4 | 66 | 65.6 | 64.8 |
| Concentration w/w (%) | 17 | 15 | 16 | 16.5 | 17 | 17.5 | 18 | 19 |
| Viscosity (cps) | | 115 | 230 | 725 | 230 | 387 | gel | gel |

Comparative Example 1. Thermally Denatured Fibrinogen Films

Comparative Example C1-A was prepared by taking Preparatory Example P1-A and adding 3.84 grams of glycerol anhydrous (J.T. Baker, USA) was added and mixed until obtaining a homogeneous solution. The solution was stored without agitation for 12 hours to allow the bubbles/foam (created by agitation) to settle. The solution was cast at a thickness of 100 micrometers onto a silicone release liner. The coated fibrinogen solution was heated at 80° C. to allow denaturation until a clear denatured fibrinogen film was obtained. A low pressure nitrogen stream was applied to the film to aid in evaporation of water.

Additional comparative examples of thermally denatured fibrinogen films, Comparative Examples C1-B and C1-C were also prepared at different glycerol concentrations (w/w to dry fibrinogen). Dissolution of the fibrinogen was completed as in example P1-A. The glycerol addition and denaturation proceeded as in example C1-A.

TABLE 2

COMPARATIVE EXAMPLES C1-A, C1-B, C1-C

|  | EXAMPLE | | |
| --- | --- | --- | --- |
|  | C1-A | C1-B | C1-C |
| Fibrinogen (g) | 5.1 | 13.6 | 13.6 |
| Deionized water (g) | 24.9 | 64.9 | 56.1 |
| Glycerol (g) | 3.84 | 1.5 | 10.26 |
| Glycerol concentration to dry fibrinogen w/w (%) | 43 | 10 | 43 |

Preparatory Example P2. Preparation of Fibrinogen Solutions with Calcium Chloride The Fibrinogen powder (Bovogen Biologicals, Australia) was analyzed by ion chromatography for citrate content and was determined to contain approximately 14 w/w % citrate. It is also estimated to contain an additional 12% sodium chloride. Sodium citrate, an anti-coagulant salt, comes with the fibrinogen powder. However, it is known from US2016/024141 that excessive salt content has a negative effect on wound healing. Preparatory Example 2 was prepared as thermally denatured fibrinogen films with the inclusion of calcium chloride. Calcium chloride was added to exchange sodium citrate to calcium citrate. The calcium chloride concentrations of Preparatory Examples P2-A and P2-B are listed below in TABLE 3. Dissolution of the fibrinogen proceeded as in example P1-A, except that calcium chloride was added after the fibrinogen and before the water. Glycerol addition and denaturation proceeded as in Comparative Example C1-A. The ingredients for Preparatory Examples P2-A and P2-B are listed below in TABLE 3.

TABLE 3

PREPARATORY EXAMPLES P2-A AND P2-B WITH VARIOUS CALCIUM CHLORIDE CONCENTRATIONS

|  | EXAMPLE | |
| --- | --- | --- |
|  | P2-A | P2-B |
| Fibrinogen (g) | 5.1 | 5.1 |
| Deionized water (g) | 24.9 | 24.9 |
| Calcium chloride (g) | 0.25 | 0.025 |
| Glycerol (g) | 3.84 | 3.84 |
| Calcium chloride concentration w/w (%) | 0.74 | 0.074 |

Example 1: Washed, De-Salted Fibrinogen Films

The dehydrated denatured fibrinogen film of Comparative Example C1-A was converted to working Example 1 by the following washing procedure to reduce the salt content in the denatured fibrinogen films. A sample of Comparative Example C1-A was soaked in 200 grams of fresh distilled water/glycerol (85/15) mixture solution for 5 minutes to form working Example 1A. A sample of Comparative Example C1-A was soaked in 200 grams of fresh distilled water/glycerol (85/15) mixture solution for 40 minutes to form working Example 1B. After the soaking step the film samples were dried at 80° C. for 30 minutes. This low salt thermal dehydrated denatured fibrinogen film of Example 1A and Example 1B was easily removed from the release liner as a flexible and transparent film.

The conductivity testing was performed by first cutting 5.1 cm×5.1 cm dry samples and placing them in glass jars with a lid and sterile water for irrigation (Baxter, Lot G122242, expiration date of March 2019) The amount of water added was such that the fibrinogen sample weight was approximately 1% by weight of the total solution. The samples were allowed to sit in the water for a minimum of 10 minutes and then the conductivity of the solution was measured.

The conductivity testing was performed using a VWR Symphony B30PCI Benctop Multi Parameter Meter—pH, Conductivity, ISE. Conductivity results for Example 1A and Example 1B and Comparative Example C1-A are shown in TABLE 4. The salt content of Comparative Example C1-A is estimated to be approximately 15 wt. % in the dried fibrinogen film with glycerol. The salt content of washed de-salted and dried Examples 1A and 1B is estimated to be approximately 2.7 wt. % and 1.6 wt. %, respectively.

TABLE 4

CONDUCTIVITY TEST RESULTS FOR WORKING EXAMPLE 1

|  | EXAMPLE | | |
| --- | --- | --- | --- |
|  | 1A | 1B | C1-A |
| Conductivity (mS/cm) | 0.55 | 0.33 | 3.07 |

Example 2. In-Vivo Evaluation of Fibrinogen Films with Low Salt Content

Low salt, washed Examples 2A and 2B may be analyzed for percent re-epithelialization according to the in-vivo re-epithelialization procedure described in 75852. Examples 2A and 2B would not irritate the wound or cause inflammation and would be expected to demonstrate an increased rate of re-epithelialization as well an increases of at least one wound healing biological marker.

What is claimed is:

1. A method of forming a fibrinogen hydrogel composition comprising:
   providing a fibrinogen hydrogel or precursor thereof, comprising fibrinogen hydrogel forming salt at a concentration greater than or equal to the threshold concentration to form the fibrinogen hydrogel;
   denaturing the fibrinogen hydrogel;
   reducing the salt concentration below the threshold concentration to form the fibrinogen hydrogel.

2. The method of claim 1, wherein the fibrinogen hydrogel precursor comprises an aqueous solution comprising fibrinogen and the fibrinogen hydrogel forming salt.

3. The method of claim 1, wherein the fibrinogen hydrogel forming salt comprises sodium citrate optionally in combination with sodium chloride.

4. The method of claim 1, wherein the threshold hydrogel forming salt concentration of the aqueous solution is at least 0.45 wt.-%.

5. The method of claim 1, wherein the fibrinogen hydrogel composition further comprises a fibrinogen hydrogel plasticizer.

6. The method of claim 5 wherein the plasticizer comprises a sugar alcohol, an alkane diol, or a combination thereof.

7. The method of claim 1, further comprising forming the fibrinogen hydrogel composition into a sheet, foam, or a plurality of pieces.

8. The method of claim 1, wherein the step of reducing the fibrinogen hydrogel forming salt concentration comprises rinsing the hydrogel with an aqueous solution.

9. The method of claim 1, further comprising dehydrating the fibrinogen hydrogel composition.

10. The method of claim 1, wherein the denaturing is accomplished by heating.

11. The method of claim 9, wherein the dehydrated denatured fibrinogen hydrogel composition has a salt concentration no greater than 20 wt.-%.

12. The method of claim 1, further comprising forming the fibrinogen hydrogel composition into a plurality of pieces.

13. The method of claim 1, further comprising combining the fibrinogen hydrogel with 0.1 to about 50 wt.-% of a carrier material.

14. The method of claim 13, wherein the carrier material comprises a water soluble polymer having a Fikentscher K-value of at least K-90.

15. The method of claim 13, wherein the carrier material comprises a polymer.

16. The method of claim 15, wherein the polymer comprises polymerized units of N-vinyl lactam polymer.

17. The method of claim 13, wherein the carrier material further comprises a swelling agent.

18. The method of claim 17, wherein the swelling agent also functions as a plasticizer for the fibrinogen hydrogel.

19. The method of claim 1, wherein reducing the salt concentration below the threshold concentration to form the fibrinogen hydrogel is before combining the fibrinogen hydrogel with a carrier material.

20. The method of claim 1, wherein reducing the salt concentration below the threshold concentration to form the fibrinogen hydrogel is after combining the fibrinogen hydrogel with a carrier material.

* * * * *